US007135463B2

(12) United States Patent
Sebti

(10) Patent No.: US 7,135,463 B2
(45) **Date of Patent: *Nov. 14, 2006**

(54) RHOB AS A SUPPRESSOR OF CANCER CELL GROWTH, CELL TRANSFORMATION, AND METASTASIS

(75) Inventor: Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/759,328

(22) Filed: Jan. 16, 2004

(65) Prior Publication Data

US 2004/0171547 A1 Sep. 2, 2004

Related U.S. Application Data

(63) Continuation-in-part of application No. 10/049,502, filed as application No. PCT/US01/19432 on Jun. 18, 2001.

(60) Provisional application No. 60/506,219, filed on Sep. 25, 2003, provisional application No. 60/212,049, filed on Jun. 16, 2000.

(51) Int. Cl.

| | |
|---|---|
| ***A61K 37/70*** | (2006.01) |
| ***A01N 43/04*** | (2006.01) |
| ***C12Q 1/68*** | (2006.01) |
| ***C12P 29/00*** | (2006.01) |
| ***C12N 15/86*** | (2006.01) |
| ***C12N 5/00*** | (2006.01) |
| ***C12N 5/08*** | (2006.01) |

(52) U.S. Cl. ........................... 514/44; 435/6; 435/455; 435/69.1; 435/456; 435/325; 435/366

(58) Field of Classification Search ................. 514/44; 435/6, 7.23, 325, 455, 320.1, 69.1

See application file for complete search history.

(56) References Cited

U.S. PATENT DOCUMENTS

2002/0034725 A1 3/2002 McKenna et al.
2003/0018003 A1 1/2003 Sebti

OTHER PUBLICATIONS

Pendergast and Rane, Farnesyltransferase inhibitors: mechanism and applications, Expert Opinion Invest Drugs, 2001, vol. 10 No. 12, pp. 2105-2116.*

Adnane, J. et al. "Suppression of Rho B expression in invasive carcinoma from head and neck cancer patients" *Clin Cancer Res*, 2002, 8:2225-2232.

Alimandi, M. et al. "Cooperative signaling of ErbB3 and ErbB2 in neoplastic transformation and human mammary carcinomas" *Oncogene*, 1995, 10:1813-1821.

Arboleda, M.J. et al. "Overexpression of AKT2/protein kinase Bβ leads to up-regulation of β1 integrins, Increased invasion, and metastasis of human breast and ovarian cancer cells" *Cancer Res*, 2003, 63:196-206.

Buday, L. and Downward, J. "Epidermal growth factor regulates p21™ through the formation of a complex of receptor, Grb2 adaptor protein, and Sos nucleotide exchange factor" *Cell*, 1993, 73:611-620.

Chen, Z. et al. "Both famesylated and geranylgeranylated RhoB inhibit malignant transformation and suppress human tumor growth in nude mice" *J Biol Chem*, 2000, 275(24):17974-17978.

Davies, M.A. et al. "Adenoviral-mediated expression of MMAC/PTEN inhibits proliferation and metastasis of human prostate cancer cells" *Clin Cancer Res*, 2002, 8:1904-1914.

Du, W. and Prendergast, G.C. "Geranylgeranylated RhoB mediates suppression of human tumor cell growth by famesyltransferase Ihibitors" *Cancer Res*, 1999, 59:5492-5496.

Du, W. et al. "Cell growth inhibition by famesyltransferase inhibitors in mediated by gain of geranylgeranylated RhoB" *Mol Cell Biol*, 1999, 19(3):1831-1840.

Forget, M.A. et al. "The expression of Rho proteins decreased with human brain tumor progression: potential tumor markers" *Clin Exp Metastasis*, 2002, 19(1):9-15, abstract.

Fritz, G. and Kaina, B. "rhoB encoding a UV-inducible Ras-related small GTP-binding protein is regulated by GTPases of the Rho family and independent of JNK, ERK, and p38 MAP kinase" *J Biol Chem*, 1997, 272(49):30637-30644.

Fritz, G. et al. "The Ras-related small GTP-binding protein RhoB is immediate-early inducible by DNA damaging treatments" *J Biol Chem*, 1995, 270(42):25172-25177.

(Continued)

*Primary Examiner*—Dave Trong Nguyen
*Assistant Examiner*—Maria Marvich
(74) *Attorney, Agent, or Firm*—Saliwanchik, Lloyd & Saliwanchik

(57) ABSTRACT

The present invention concerns the use of the protein RhoB and its variants to inhibit cancer cell growth, migration, invasion, metastasis, malignant cell transformation, and/or to modulate oncogenic signaling, wherein introducing RhoB directly, or indirectly via a nucleic acid sequence encoding RhoB, into a malignantly transformed cell or a cancerous cell decreases phosphorylation of Erk and Akt proteins inhibiting the PI3-kinase/Akt cell survival pathway and promoting apoptotic cell death. In one aspect, the compositions and methods of the present invention are used to inhibit the malignant transformation of cells by the oncogenes H-Ras, N-Ras, K-Ras, EGFR, or ErbB2, or to inhibit the growth of cancer cells transformed by such oncogenes. The compositions and methods of the present invention may be used to inhibit cancer cell growth, inhibit malignant cell transformation, and modulate oncogenic signaling in vivo or in vitro.

16 Claims, 19 Drawing Sheets

OTHER PUBLICATIONS

Hall, A. "Rho GTPases and the actin cytoskeleton" *Science*, 1998, 279(5350):509-514.

Hunter, T. "Oncoprotein networks" *Cell*, 1997, 88:333-346.

Jahner, D. and Hunter, T. "The ras-related gene rhoB is an immediate-early gene inducible by v-Fps, epidermal growth factor, and platelet-derived growth factor in rat fibroblasts" *Mol Cell Biol*, 1991, 11(7):3682-3690.

Jiang, K. Et al. "Regulation of Akt-dependent cell survival by Syk and Rac" *Blood*, 2003, 101:236-244.

Khosravi-Far, R. and Der, C.J. "The Ras signal transduction pathway" *Cancer Metastasis Rev*, 1994, 13:67-89.

Khosravi-Far, R. et al. "Activation of Rac1, RhoA, and mitogen-activated protein kinases Is required for Ras transformation" *Mol Cell Biol*, 1995, 15(11):6443-6453.

Kim, D. et al. "Akt/PKB promotes cancer cell invasion via increased motility and metalloproteinase production" *Faseb J*, 2001, 15:1953-1962.

Kubiatowski, T. et al. "Association of increased phosphatidylinositol 3-kinase signaling with increased invasiveness and gelatinase activity in malignant gliomas" *J Neurosurg*, 2001, 95:480-488.

Lebowitz, P.F. et al. "Evidence that famesyltransferase inhibitors suppress Ras transformation by interfering with Rho activity" *Mol Cell Biol*, 1995, 15(12):6613-6622.

Lui, A. et al. "RhoB alteration is necessary for apoptotic and antineoplastic responses to famesyltransferase inhibitors" *Mol Cell Biol*, 2000, 20(16):6105-6113.

Liu, A. et al. "RhoB is required to mediate apoptosis in neoplastically transformed cells after DNA damage" *Proc Natl Acad Sci USA*, 2001, 98(11):6192-6197.

Luetteke, N.C. et al. "The mouse waved-2 phenotype results from a point mutation in the EGF receptor tyrosine kinase" *Genes Dev*, 1994, 8:399-413.

Nakamura, T. et al. "Cloning of the RhoB gene from the mouse genome and characterization of its promoter region" *Biochem. Biophys. Res. Commun.*, 1996, 226(3):688-694, abstract.

Park, B-K. et al. "Akt1 induces extracellular matrix invasion and matrix metalloproteinase-2 activity in mouse mammary epithelial cells" *Cancer Res*, 2001, 61:7647-7653.

Pruitt, K. and Der, C.J. "Ras and Rho regulation of the cell cycle and oncogenesis" *Cancer Lett.*, 2001, 171(1):1-10.

Quilliam, L.A. et al. "Identification of residues critical for Ras(17N) growth-inhibitory phenotype and for Ras interaction with guanine nucleotide exchange factors" *Mol Cell Biol*, 1994, 14(2):1113-1121.

Stewart, A.L. et al. "P13K blockade by Ad-PTEN inhibits invasion and induces apoptosis in radial growth phase and metastatic metanoma cells" *Mol Med*, 2002, 8(8):451-461.

Symons, M. and Settleman, J. "Rho family GTPases: more than simple switches" *Trends Cell Biol*, 2000, 10(10):415-419.

Turkson, J. et al. "Requirement for Ras/Rac1-mediated p38 and c-Jun N-terminal kinase signaling in Stat3 transcriptional activity induced by the Src oncoprotein" *Mol Cell Biol*, 1999, 19(11):7519-7528.

Van Aelst, L. and D'Souza-Schorey, C. "Rho GTPases and signaling networks" *Genes Dev*, 1997, 11(18):2295-2322.

Vlahos, C.J. et al. "A specific inhibitor of phosphatidylinositol 3-kinase, 2-(4-morpholinyl)-8-phenyl-4H-1-benzopyran-4-one (LY294002)" *J Biol Chem*, 1994, 269(7):5241-5248.

Yano, H. et al. "Biochemical and pharmacological studies with KT7692 and LY294002 on the role of phosphatidylinositol 3-kinase in FcεRl-mediated signal transduction" *Biochem J*, 1995, 312(Pt 1):145-150.

Zohn, I.M. et al. "Rho family proteins and Ras transformation: the RHOad less traveled gets congested" *Oncogene*, 1998, 17:1415-1438.

McCormick, F. *Nature*, 1993, 363:15-16.

Campbell, S.L. et al. *Oncogene*, 1998, 17:1395-1413.

Barbacid, M. *Annu. Rev. Biochem.*, 1987, 56:779-827.

Bos, J.L. *Cancer Res.*, 1989, 49:4682-4689.

Olson, M.F. et al. *A. Science*, 1995, 269:1270-1272.

Qui, R.G. et al. *Nature*, 1995, 374:457-459.

Mellor, H. et al. *J. Biol. Chem.*, 1998, 273:4811-4814.

Zhang, F.L. et al. *Annu. Rev. Biochem.*, 1996, 65:241-269.

Lebowitz, P.F. et al. *J. Biol. Chem.*, 1997, 272:15591-15594.

Sebti, S.M. et al. *Pharmacol. Ther.*, 1997, 272:15591-15594.

Gibbs, J.B. et al. *Annu. Rev. Pharmacol. Toxicol.*, 1997, 37:143-166.

Cox, A.D. et al. *Biochim. Biophys. Acta.*, 1997, 1333:F51-F71.

Lebowitz, P.F. et al. *Oncogene*, 1998, 17:1439-1445.

Chen, Z. et al. "Famesylated and geranylgeranylated RhoB suppress the transformation of PANC-1 human pancreatic cancer cells" Proceedings of the 91st Annual Meeting of the American Association of Cancer Research, vol. 14, p. 220, abstract No. 1402.

Liu and Jessell "A role for rhoB in the detamination of neural crest cells from the dorsal beural tube" *Development*, 1998, 125:5055-5067.

Lebowitz et al. "Famesyltransferase inhibitors alter the prenylations and growth-stimulating function of RhoB" *JBC*, 1997, 272(25):15591-15594.

Meng and El-Deiry "Tumor suppressor genes as targets for cancer gene therapy" *Gene Therapy of Cancer*, Chapter 1, pp. 3-18.

Verma and Somia "Gene therapy-promises, problems and prospects" *Nature*, 1997, 389-239-242.

Marshall "Second child in French trial is found to have aleukemia" *Science*, 2003, 299-320.

Torchilin and Lukyanov "Peptide and protein drug delivery to and into tumors: challenges and solutions" *Drug Discover Today*, 2003, 8:259-265.

U.S. Appl. No. 11/274,368, filed Nov. 14, 2005, Sebti.

Sun, J. et al. "Antitumor efficacy of a novel class of non-thiol-containing peptidomimetic inhibitors of famesyltransferase and geranylgeranyltransferase I: Combination therapy with the cytotoxic agents cisplatin, taxol, and gemcitabine" *Cancer Res.*, 1999, 59:4919-4926.

Adamson, P. et al. "Post-translational modifications of $p21^{rho}$ proteins" *J Biol Chem*, 1992, 267:20033-20038.

Adnane, J. et al. "RhoB, not RhoA, represses the transcription of the transforming growth factor β type II receptor by a mechanism involving activator protein 1" *J. Biol Chem*, 2002, 277:8500-8507.

Armstrong, S.A. et al. "CAAX geranylgeranyl transferase transfers famesyl as efficiently as geranylgeranyl to RhoB" *J Biol Chem*, 1995, 270:7864-7868.

Baron, R. et al. "RhoB prenylation is driven by the three carboxylterminal amino acids of the protein: Evidenced *in vivo* by an anti-farnesyl cysteine antibody" *Proc Natl Acad Sci USA*, 2000, 97:11626-11631.

Chang, F. et al. "Signal transduction mediated by the Ras/Raf/MEK/ERK pathway from cytokine receptors to transcription factors: potential targeting for therapeutic intervention" *Leukemia*, 2003, 17:1263-1293.

Chardin, P. et al. "Coding sequence of human rho cDNAs clone 6 and clone 9" *Nucleic Acids Res.* 1988, 16:2717.

Clark, E.A. et al. "Genomic analyis of metastasis reveals an essential role for RhoC" *Nature*, 2000, 406:532-535.

Downward, J. "Targeting Ras signaling pathways in cancer therapy" *Nat Rev Cancer*, 2003, 3:11-22.

Forget, M.A. et al. "the expression of Rho proteins decreases with human brain tumor progression: potential tumor markers" *Clin Exp Metastasis*, 2002, 19(1):9-15.

Fritz, G. and Kaina, B. "Ras-related GTPase RhoB represses NF-kB signaling" *J Biol Chem*, 2001, 276:3115-3122.

Fukata, M. et al. "Roles of Rho-family GTPases in cell polarisation and directional migration" *Curr Opin Cell Biol*, 2003, 15:590-597.

Genbank accession No. X06820, "*H. sapiens* rhoB gene mRNA" Oct. 24, 1996.

Genbank accession No. CAA29968, "rhoB [*Homo sapiens*]" Oct. 24, 1996.

Jiang, K. et al. "Akt mediates Ras downregulation of RhoB, a suppressor of transformation, invasion, and metastasis" *Mol Cell Biol*, 2004, 24:5565-5576.

Jiang, K. et al. "EGFR, ErbB2 and Ras but not Src suppress RhoB expression while ectopic expression of RhoB antagonizes oncogene-mediated transformation" *Oncogene*, 2004, 23:1136-1145.

Lebowitz, P.F. et al. "Prenylation of RhoB is required for its cell transforming function but not its ability to activate serum response element-dependent transcription" *J Biol Chem*, 1997, 272:16093-16095.

Liu, A-X. et al. "RhoB is dispensable for mouse development, but it modifies susceptibility to tumor formation as well as cell adhesion and growth factor signaling in transformed cells" *Mol Cell Biol*, 2001, 21:6906-6912.

Mazieres, J. et al. "Loss of RhoB expression in human lung cancer progression" *Clin Cancer Res*, 2004, 10:2742-2750.

Nakamura, T. et al. "Cloning of the RhoB gene from the mouse genome and characterization of its promoter region" *Biochem. Biophys. Res. Commun.*, 1996, 226(3):688-694.

Nobes, C.D. and Hall, A. "Rho, Rac, and Cdc42 GTPases regulate the assembly of multimolecular focal complexes associated with actin stress fibers, lamellipodia, and filopodia" *Cell*, 1995, 81:53-62.

Sebti, S.M. and Hamilton, A.D. "Inhibition of Ras prenylation: A novel approach to cancer chemotherapy" 1997, 74:103-114.

Symons, M. and Rusk, N. "Control of vesicular trafficking by Rho GtPases" *Curr Biol*, 2003, 13:R409-418.

Wang, D-A and Sebti, S.M. "Palmitoylated cysteine 192 is required for RhoB tumor suppressive and apoptotic activities" Presentation at the American Association for Cancer Research, Anaheim, CA, Apr. 16-20, 2005, abstract.

Wang, D-A. and Sebti, S.M. "Palmitoylated cysteine 192 is required for RhoB tumor-suppressive and apoptotic activities" *J. Biol. Chem.*, 2005, 280:19243-19249.

Welsh, C.F. "Rho GTPases as key transducers of proliferative signals in G, cell cycle regulation" *Breast Cancer Res Treat*, 2004, 84:33-42.

Adjei, A.A. "Ras signaling pathway proteins as therapeutic targets" *Curr Pharm Design*, 2001, 7:1581-1594.

Caponigro, F. "Famesyl transferase inhibitors: a major breakthrough in anticancer therapy?" *Anti-Cancer Drugs*, 2002, 13:891-897.

End, D.W. et al. "Characterization of the antitumor effects of the selective farmesyl protein transferase inhibitor R115777 *in vivo* and *in vitro" Cancer Res.*, 2001, 61:131-137.

Gura, T. "Systems for identifying new drugs are often faulty" *Science*, 1997, 278:1041-1042.

Kerbel, R.S. "Human tumor xenografts as predictive preclinical models for anticancer drug activity in humans" *Cancer Biol. & Ther.*, 2003, 2(4 Supp. 1):S134-S139.

Reuter, C.W. et al. "Targeting the Ras signaling pathway: a rational, mechanism-based treatment for hematologic malignancies?"*Blood*, 2000, 96:1655-1669.

Robson, T. and Hirst, D. "Transcriptional targeting in cancer gene therapy" *J. Biomed. Biotech.*, 2003, 2:110-137.

Shi, B. et al. "The famesyl protein transferase inhibitor SCH66336 synergizes with taxanes in vitro and enhances their antitumor activity in vivo" *Cancer. Chemother. Pharmacol.*, 2000, 46:387-393.

Voskoglou-Nomikos, T. et al. "Clinical predictive value of the *in vitro* cell line, human xenograft, and the mouse allograft preclinical cancer models" *Clin. Cances Res.*, 2003, 9:4227-4239.

Qiu, R.G. et al. *Nature*, 1935, 374:457-459.

Mellor, H. et al. *J. Biol. Chem.*, 1998, 273:4811-4814.

Zhang, F.L. et al. *Annu. Rev. Biochem.*, 1998, 65:241-269.

Lebowitz, P.F. et al. *J. Biol. Chem.*, 1997, 272:15591-15594.

Sebti, S.M. et al. *Pharmacol. Ther.*, 1997, 272:15591-15594.

Gibbs, J.B. et al. *Annu. Rev. Pharmacol. Toxicol.*, 1997, 37:143-166.

Cox, A.D. et al. *Biochim. Biophys. Acta.*, 1997, 1333:F51-F71.

Lebowitz, P.F. et al. *Oncogene*, 1998, 17:1439-1445.

Chen, Z. et al. "Famesylated and geranylgeranylated RhoB suppress the transformation of PANC-1 human pancreatic cancer cells" Proceedings of the 91$^{st}$ Annual Meeting of the American Association of Cancer Research, vol. 14, p. 220, abstract No. 1402, 2000.

Liu and Jessell "A role for rhoB in the detamination of neural crest cells from the dorsal beural tube" *Development*, 1998, 125:5055-5067.

Lebowitz et al. "Famesyltransferase Inhibitors alter the prenylations and growth-stimulating function of RhoB" *JBC*, 1997, 272(25):15591-15594.

Meng and El-Deiry "Tumor suppressor genes as targets for cancer gene therapy" *Gene Therapy of Cancer*, Chapter 1, pp. 3-18, 1999.

Verma and Somia "Gene therapy-promises, problems and prospects" *Nature*, 1997, 389:239-242.

* cited by examiner

FIG. 1A
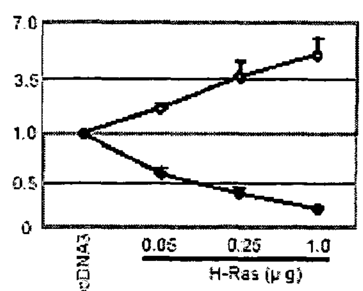
FIG. 1B
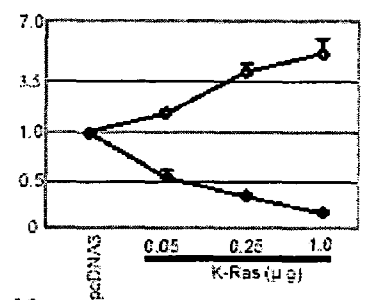
FIG. 1C
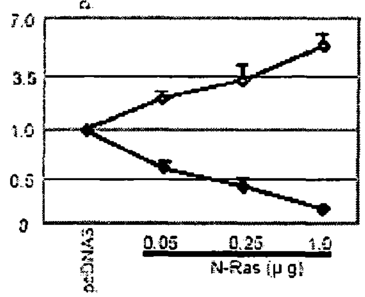
FIG. 1D
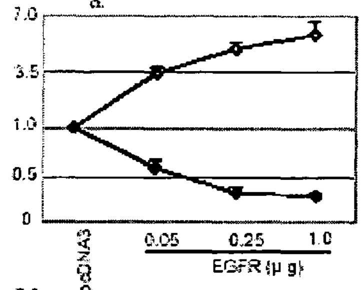
FIG. 1E
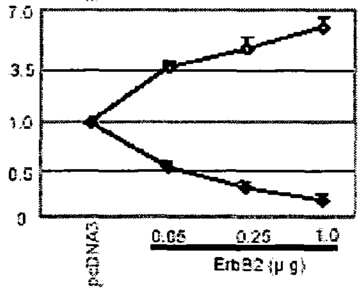
FIG. 1F
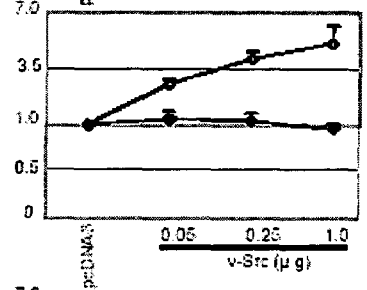
FIG. 1G
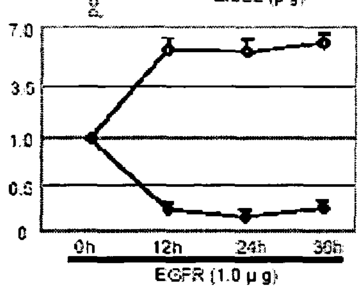
FIG. 1H
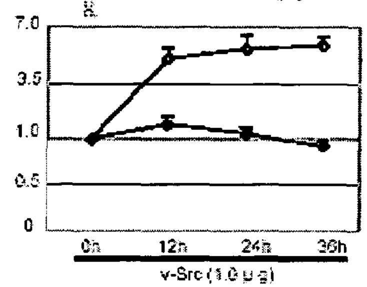
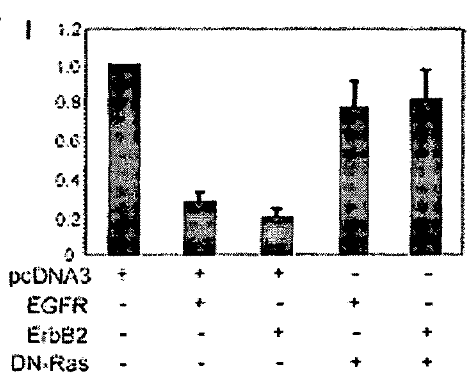
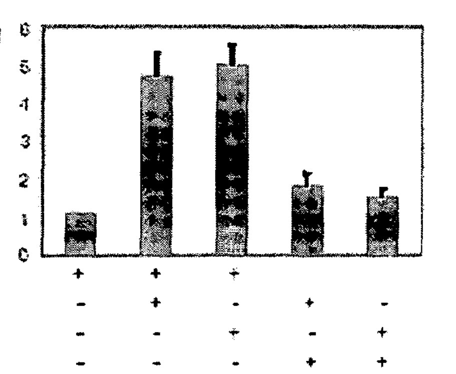
| | I | | | | | J | | | | |
|---|---|---|---|---|---|---|---|---|---|---|
| pcDNA3 | + | + | + | - | - | + | + | + | | |
| EGFR | - | + | - | + | - | - | + | - | + | - |
| ErbB2 | - | - | + | - | + | - | - | + | - | + |
| DN-Ras | - | - | - | + | + | - | - | - | + | + |
FIG. 1I
FIG. 1J

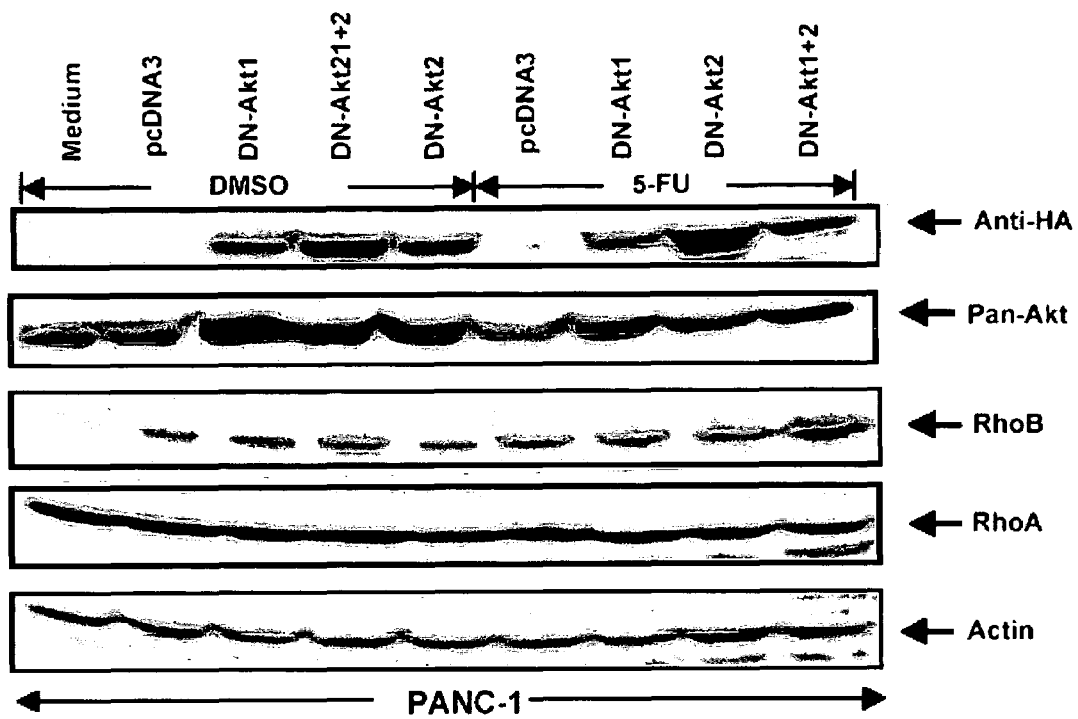
FIG. 7D
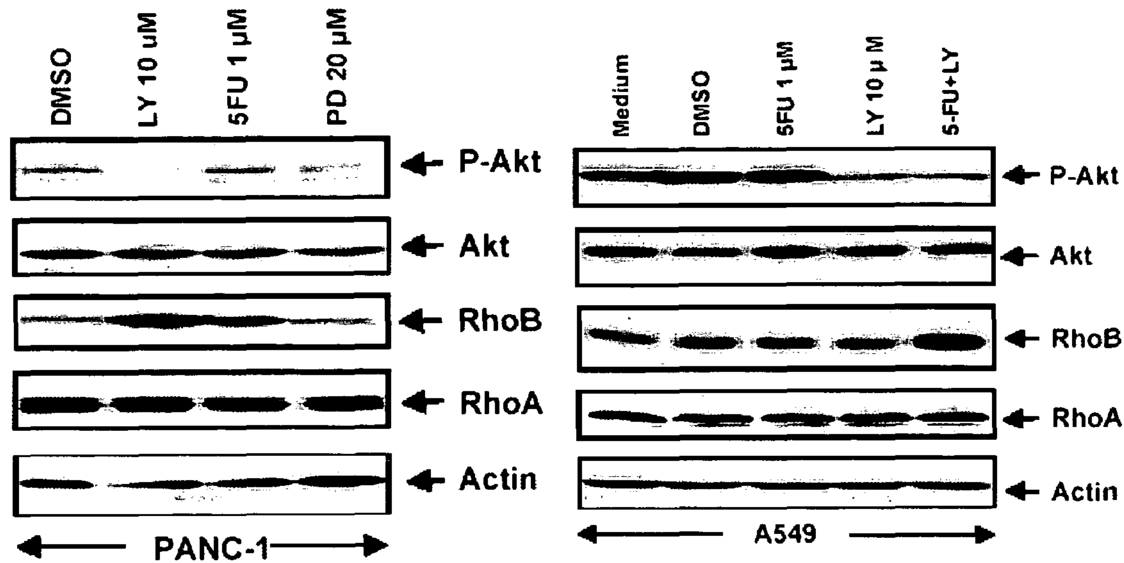
FIG. 7E
FIG. 7F

RHOB AS A SUPPRESSOR OF CANCER CELL GROWTH, CELL TRANSFORMATION, AND METASTASIS

CROSS-REFERENCE TO RELATED APPLICATIONS

The present application claims the benefit of U.S. Provisional Application Ser. No. 60/506,219, filed Sep. 25, 2003; and is a continuation-in-part of U.S. application Ser. No. 10/049,502, filed Feb. 13, 2002, which is a national stage §371 filing of International Application No. PCT/US01/19432, filed Jun. 18, 2001, which claims the benefit of U.S. Provisional Application Ser. No. 60/212,049, filed Jun. 16, 2000, which are hereby incorporated by reference herein in their entirety, including any figures, tables, nucleic acid sequences, and amino acid sequences.

The subject invention was made with government support under a research project supported by the National Institutes of Health grant no. CA67771. The Federal Government may have certain rights in this invention.

BACKGROUND OF THE INVENTION

Low molecular weight guanosine triphosphate (GTP)/guanosine diphosphate (GDP) binding GTPases are signal transducers that play a central role in many important cellular functions including cytoskeleton organization, proliferation, differentiation, and development (Khosravi-Far, R. and Der, C. J., *Cancer Metastasis Rev,* 1994, 13:67–89; Zohn, I. M. et al., *Oncogene,* 1998, 17:1415–38). Some of these small G-proteins have also been involved in pathological conditions such as malignant transformation. For example, Ras, RhoA, Rac1 and cdc42 have been implicated in oncogenesis, invasion and metastasis (Hall, A., *Science,* 1998, 279:509–14; Khosravi-Far, R. and Der, C. J., *Cancer Metastasis Rev,* 1994, 13:67–89; Pruitt, K. and Der, C. J., *Cancer Lett,* 2001, 171:1–10; Symons, M. and Settleman, J., *Trends Cell Biol,* 2000, 10:415–9; Van Aelst, L. and D'Souza-Schorey, C., *Genes Dev,* 1997, 11:2295–322). In contrast, a closely related family member, RhoB, which shares 86% amino acid sequence identity with RhoA, has recently been shown to have tumor suppressive activity (Chen, Z. et al., *J Biol Chem,* 2000, 275:17974–8; Du, W. et al., *Mol Cell Biol,* 1999, 19:1831–40; Du, W. and Prendergast, G. C., *Cancer Res,* 1999, 59:5492–6).

Though highly homologous, RhoA and RhoB are distinct in several aspects. While RhoA is constitutively expressed, RhoB is inducible and has been characterized as an early-response gene. RhoB is known to be induced by DNA damaging agents such as UV and γ-irradiation, N-methyl-N-nitrosourea and cisplatin as well as other chemicals such as methyl methansulfonate, hydrogen peroxide ($H_2O_2$) and cycloheximide, and growth factors such as EGF and PDGF (Fritz, G. and Kaina, B., *J Biol Chem,* 1997, 272:30637–44; Fritz, G. et al., *J Biol Chem,* 1995, 270:25172–7; Jahner, D. and Hunter, T., *Mol Cell Biol,* 1991, 11:3682–90). Furthermore, unlike RhoA that has a half life of 24 hours, RhoB's half life is much shorter and is on the order of 1–2 hours (Lebowitz, P. F. et al., *Mol Cell Biol,* 1995, 15:6613–22). Finally, while RhoA mediates oncogenesis, RhoB has tumor suppressive activity, and it has been shown to inhibit tumor cell proliferation in rodent fibroblasts as well as human cancer cells (Chen, Z. et al., *J Biol Chem,* 2000, 275:17974–8; Du, W. et al., *Mol Cell Biol,* 1999, 19:1831–40; Du, W. and Prendergast, G. C., Cancer Res, 1999, 59:5492–6). RhoB also inhibits oncogenic and tumor survival pathways and induces apoptosis in vitro and inhibits the growth of human tumors grown in nude mice (Chen, Z. et al., *J Biol Chem,* 2000, 275:17974–8). Furthermore, targeted deletion of RhoB results in mice that are more sensitive to skin carcinogenesis (Liu, A. et al., *Mol Cell Biol,* 2000, 20:6105–13). Ras-transformed RhoB (−/−) fibroblasts from these mice are resistant to γ-irradiation-, doxorubicin-, and TAXOL-induced apoptosis (Liu, A. et al., *Proc Natl Acad Sci USA,* 2001, 98:6192–7). Finally, RhoB expression levels have been recently shown to dramatically decrease with the aggressiveness of tumors in head, neck and brain cancer patients (Adnane, J. et al., *Clin Cancer Res,* 2002, 8:2225–32; Forget, M. A. et al., *Clin Exp Metastasis,* 2002, 19:9–15).

BRIEF SUMMARY OF THE INVENTION

The present invention pertains to methods of inhibiting the growth of a cancerous cell by contacting the cell with an effective amount of a RhoB protein, or a variant of the RhoB protein.

The present invention concerns the use of the protein RhoB, or a variant thereof, to inhibit cancer cell growth, metastasis, invasion, migration, malignant cell transformation, and/or to modulate oncogenic signaling. According to the methods of the present invention, RhoB is introduced directly, or indirectly via a nucleic acid sequence encoding RhoB, into a malignantly transformed cell or a cancerous cell, wherein RhoB decreases phosphorylation of Erk and Akt proteins inhibiting the PI3-kinase/Akt cell survival pathway and promoting apoptotic cell death. Therefore, the desirable goals of promoting apoptosis ("programmed cell death") of selective cancerous cells and suppression of malignant transformation of normal cells within a patient are likewise accomplished through administration of RhoB, or a variant thereof, which can be administered as a simple compound or in a pharmaceutical composition. RhoB (or a variant thereof) can be used alone or in combination with additional anti-cancer agents, such as cytotoxic agents (e.g., 5-flurouracil, TAXOL) and/or anti-signaling agents (e.g., the PI3K inhibitor LY).

BRIEF DESCRIPTION OF THE DRAWINGS

FIGS. 1A–1J show that oncogenic H-Ras, K-Ras, N-Ras, EGFR, ErbB2, but not v-Src suppress RhoB promoter transcriptional activity in NIH3T3 cells: Ras is required for EGFR and ErbB2 suppression of RhoB. NIH3T3 cells were transiently transfected with various oncogene constructs (FIG. 1A: H-Ras, FIG. 1B: K-Ras, FIG. 1C: N-Ras, FIG. 1D and FIG. 1G: EGFR, FIG. 1E: ErbB2, FIG. 1F and FIG. 1H: v-Src) along with full length RhoB promoter-firefly luciferase reporter and SRE-Renilla luciferase reporter for 36 hrs (β-gal was used as an internal control) as described in the Materials and Methods section. EGFR or ErbB2 (FIG. 1I and FIG. 1J) were also co-transfected with dominant negative N17-H-Ras in addition to the reporter gene constructs. Cell lysates were processed for determination of RhoB and SRE promoter activity by luminescence as described in the Luciferase assay kit (Promega). The data are reported as ratios of Luci/β-gal from the cells transfected by the oncogene(s) over those from pcDNA3-transfected cells.

As shown in FIG. 6A, NIH3T3 cells were transiently transfected with RhoB-promoter luci and SRE-luci constructs in the presence or absence of H-Ras61L, CA-PI3K, or CA-Akt for 24 hours, then the cells were treated by either DMSO, or 2.0 μM 5-FU for another 12 hours. The cell lysates were processed as in FIGS. 5A–5D. H-Ras/3T3 cells (FIG. 6B) and A549 cells (FIG. 6D) were transiently transfected with RhoB-promoter luciferase and SRE-luciferase constructs and cultured for 24 hours; the cells were then treated by either DMSO, or LY294002 or 5-FU or LY294002 plus 5-FU for 12 hours. The cell lysates were processed as in FIGS. 5A–5D. PANC-1 cells (FIG. 6C) were transiently transfected with CA-PI3K, or CA-Akt, or pcDNA3 vector control for 24 hours, then treated by either DMSO, or LY294002 or 5-FU or LY294002 plus 5-FU for 12 hours. The cell lysates were processed as in FIGS. 5A–5D.

FIGS. 7A–7F show that blocking H-Ras/PI3K/Akt pathway induces RhoB expression in NIH3T3 cells and human cancer cell lines. H-Ras/3T3 cells were treated with (FIG. 7A) different concentrations of LY294002 for 48 hrs or (FIG. 7B) LY294002 (20 μM) for different time intervals. The cells were then lysed and analyzed for RhoB and RhoA protein levels by Western Blotting with anti-RhoB and anti-RhoA; the same filter was re-probed with antiβ-actin for loading control. NIH3T3 cells (FIG. 7C) were transiently transfected with various genes as indicated for 24 hours; and then treated with either DMSO vehicle or LY294002 or 5-FU alone or in combination for another 48 hours. The cells were analyzed for RhoB, RhoA, and 13-actin protein levels as described above. PANC-1 cells (FIG. 7D) were transiently transfected with DN-Akt1 and DN-Akt2 genes as indicated for 24 hours; and then treated with either DMSO vehicle or 5-FU alone or in combination for another 48 hours. The cells were analyzed for RhoB and RhoA protein levels by Western Blotting with anti-RhoB and anti-RhoA; the same filter was re-probed with anti-β-actin, anti-HA and anti-pan-Akt antibodies. PANC-1 cells (FIG. 7E) and A549 cells (FIG. 7F) were treated PD, LY or 5-FU as indicated for 48 hours; then analyzed for RhoB and RhoA protein levels by Western Blotting as described above.

In FIG. 10B, the bars at each time point (0, 12, 24 hrs), left-to-right, correspond to PCD, H-Ras, AKT, RhoA, RhoB, Akt+RhoA, and Akt+RhoB, respectively. B16-F10 melanoma cells were transiently transfected with pcDNA3 vector, pcDNA-RhoA or pcDNA-RhoB; 20 hours later, the cells were examined for gene delivery by Western Blotting with anti-HA, as shown in FIG. 10C. $5\times10^5$ of the cells from FIG. 10A were injected into the tail veins of C57/B16 mice. The metastatic nodules growing in the lungs were counted and photographed at 26 days, as shown in FIG. 10D. The numbers of metastatic nodules per mouse lung represent an average±standard error from 5 mice per group. FIG. 10E is a scheme demonstrating an antagonistic interaction between the oncogenic Ras/PI3K/Akt tumor survival pathway and RhoB. Based on the results described herein, it is proposed tumor cells may have to downregulate RhoB expression, and thus suppress its ability to inhibit transformation, invasion and metastasis as one of the steps necessary for reaching a highly malignant phenotype (FIG. 10E).

DETAILED DISCLOSURE OF THE INVENTION

Figure 2A:
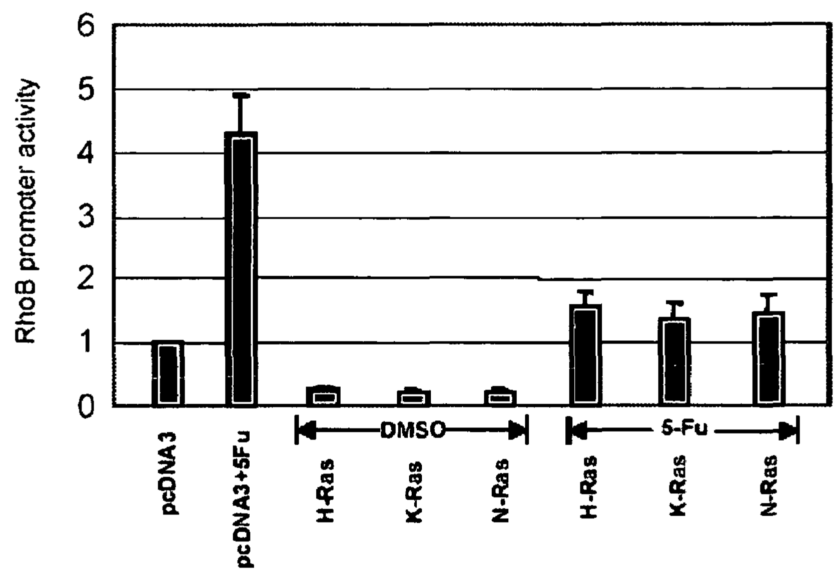
FIGS. 2A–2C show that the ability of 5-FU to induce RhoB promoter activity and protein levels is antagonized by oncogenic H-, K- and N-Ras in NIH3T3 cells. NIH3T3 cells were transiently transfected with RhoB promoter luciferase and SRE-luciferase constructs in the presence or absence of Ras oncogenes for 24 hrs, then the cells were treated by either DMSO, or 2.0 μM 5-FU for another 12 hrs. The cell lysates were processed, calculated and the results, shown in FIG. 2A, are reported as described in FIGS. 1A–1J. NIH3T3 cells were transiently transfected with various oncogenes or pcDNA3 vector control and cultured for 36 hrs; the pcDNA3-transfected cells were treated by either DMSO or 5-FU for 36 hrs. The cells were then lysed and analyzed for transfection efficiency by Western blotting with anti-HA or anti-Src antibody and for RhoB protein level with anti-RhoB antibody. Results are shown in FIG. 2B. β-actin was detected as an internal control. NIH3T3 cells were transiently transfected with various Ras oncogenes or pcDNA3 vector control for 12 hrs, then treated by either DMSO, or 5-FU for another 36 hrs. The whole cell lysates were analyzed for RhoB protein level by Western blotting with anti-RhoB antibody. Results are shown in FIG. 2C. β-actin was detected as an internal control.

In one aspect, the present invention provides a method of inhibiting the growth of a cancerous cell(s) by contacting the cell(s) with an effective amount of RhoB protein, or a variant thereof. The method of the present invention is useful for inhibiting the migration, invasion, and/or metastasis of cancer cells transformed by an oncogene other than v-src, such as H-Ras, N-Ras, K-Ras, EGFR, and ErbB2. The method of the present invention is useful for inhibiting malignant transformation of normal cells by these oncogenes. Optionally, the cancerous cell(s) can be contacted with RhoB (or a variant thereof) in combination (simultaneously or consecutively in any order) with one or more additional anti-cancer agents, such as cytotoxic agents (e.g., 5-flurouracil, TAXOL) and/or anti-signaling agents (e.g., the PI3K inhibitor LY). Advantageously, the RhoB (or a variant thereof) can sensitize the cancerous cell(s) to the activity of the anti-cancer agent. For example, the RhoB (or a variant thereof) can act as a sensitizer to anti-cancer drug-induced apoptosis, or other anti-cancer activity.

The term “RhoB protein or a variant thereof” denotes RhoB-F, RhoB-GG and RhoB-WT proteins and any variants thereof that may be derived from RhoB-F, RhoB-GG or RhoB-WT as variants possessing at least one characteristic biological activity of RhoB, derived, for example, from the aforementioned proteins by truncation, oxidation, amino acid substitution, post-translational modification, labeling, or by linkage to another molecule.

By inhibiting the growth of cancer cells, the methods and compositions of the present invention can be used to treat a number of cancers including, but no limited to, leukemias and lymphomas, such as acute lymphocytic leukemia, acute non-lymphocytic leukemias, chronic lymphocytic leukemia, chronic myelogenous leukemia, Hodgkin’s Disease, non-Hodgkin’s lymphomas, and multiple myeloma, childhood solid tumors such as brain tumors, neuroblastoma, retinoblastoma, Wilms’ Tumor, bone tumors, and soft-tissue sarcomas, common solid tumors of adults such as lung cancer, colon and rectum cancer, breast cancer, prostate cancer, urinary cancers, uterine cancers, bladder cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The methods of the subject invention can be carried out in vivo or in vitro, to inhibit the growth of cancerous cells in humans and non-human mammals.

In another aspect, the present invention provides a method of inhibiting malignant transformation of a cell. In this embodiment, RhoB or a variant thereof, a composition comprising RhoB, or a variant of RhoB, or a pharmaceutically acceptable salt of RhoB or a variant thereof, is administered to a cell capable of malignant transformation, thereby inhibiting transformation. The method of the invention may prevent malignant transformation of the cell.

As demonstrated herein, the present invention further provides a method of inducing apoptosis in a transformed cell. In this embodiment, RhoB or a variant thereof, a composition comprising RhoB, a variant of RhoB, or a pharmaceutically acceptable salt thereof, is administered to a transformed cell, thereby promoting apoptosis.

In another aspect, the present invention therefore provides a method of inhibiting oncogenic signaling in a cell, and a method for decreasing phosphorylated protein such as Akt, Erk1, or Erk2 in a transformed cell, comprising administering to the cell a composition comprising RhoB, a variant of RhoB, or a pharmaceutically acceptable salt thereof.

The methods of the present invention, for example, for inhibiting the growth of a cancerous cell, can be advantageously combined with at least one additional therapeutic method, including but not limited to chemotherapy, radiation therapy, therapy that selectively inhibits Ras oncogenic signaling, or any other therapy known to those of skill in the art of the treatment and management of cancer, such as administration of an anti-cancer agent.

The methods of the present invention can be performed by introducing a nucleic acid construct encoding the RhoB protein or a variant thereof into the cell, whereby the nucleic acid is expressed and the RhoB protein, or variant thereof, is made within the cell from the construct. The term "nucleic acid construct" refers to an assembly which is capable of directing the expression of the sequence(s) or gene(s) of interest. The construct preferably includes transcriptional promoter/enhancer or locus defining element(s), or other elements which control gene expression by other means such as alternate splicing, nuclear RNA export, post-translational modification of messenger, or post-transcriptional modification of protein. In addition, the construct preferably includes a sequence which, when transcribed, is operably linked to the sequence(s) or gene(s) of interest and acts as a translation initiation sequence. Optionally, the vector construct may also include a signal which directs polyadenylation, a selectable marker such as Neo, TK, hygromycin, phleomycin, histidinol, or DHFR, as well as one or more restriction sites and a translation termination sequence. In addition, if the vector construct is placed into a retrovirus, the vector construct preferably includes a packaging signal, long terminal repeats (LTRs), and positive and negative strand primer binding sites appropriate to the retrovirus used (if these are not already present).

Within one embodiment, a recombinant viral vector (preferably, but not necessarily, a recombinant adenovirus) carries a vector construct containing a RhoB or variant RhoB encoding nucleic acid sequence operably linked with an event-specific promoter, such as a cell cycle-dependent promoter (e.g., human cellular thymidine kinase or transferrin receptor promoters), which will be transcriptionally active primarily in rapidly proliferating cells, such as tumors. In this manner, rapidly replicating cells which contain factors capable of activating transcription from these promoters are preferentially destroyed by the RhoB or variant RhoB produced by the vector construct.

Administration of RhoB as a salt may be carried out. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The protein variants of RhoB or nucleic acids that encode them can be formulated as pharmaceutical compositions and administered to a patient, such as a human patient, in a variety of forms adapted to the chosen route of administration, i.e., orally or parenterally, by intravenous, intramuscular, topical or subcutaneous routes, or via electroporation, or transformation. Additionally, naked DNA, or via virally mediated administration may be employed.

Thus, the RhoB or RhoB variants (i.e., polypeptides or polynucleotides encoding the polypeptides) may be systemically administered, e.g., orally, in combination with a pharmaceutically acceptable vehicle (i.e., carrier) such as an inert diluent or an assimilable edible carrier. They may be enclosed in hard or soft shell gelatin capsules, may be compressed into tablets, or may be incorporated directly with the food of the patient's diet. For oral therapeutic administration, the RhoB or RhoB variants may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of RhoB or RhoB variant in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the RhoB or RhoB variant, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the RhoB or RhoB variant (i.e., polypeptides or polynucleotides encoding the polypeptides) may be incorporated into sustained-release preparations and devices.

The active agent (i.e., RhoB polypeptides or RhoB variant polypeptides, or polynucleotides encoding the polypeptides) may also be administered intravenously or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating RhoB or RhoB variant (i.e., polypeptides or polynucleotides encoding the polypeptides) in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the RhoB or RhoB variant may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the RhoB or RhoB variants can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the RhoB or RhoB variant to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the active agent in a liquid composition, such as a lotion, will be from about 0.1–25 wt.-%, preferably from about 0.5–10 wt.-%. The concentration in a semi-solid or solid composition such as a gel or a powder will be about 0.1–5 wt.-%, preferably about 0.5–2.5 wt.-%. Single dosages for injection, infusion or ingestion will generally vary between 5–1500 mg, and may be administered, i.e., 1–3 times daily, to yield levels of about 0.1–50 mg/kg, for adults. A preferred dosage of the present invention is between 7.5 to 45 mg per day, administered orally, with appropriate adjustment for the body weight of an individual.

Accordingly, the present invention includes a pharmaceutical composition comprising RhoB or RhoB variants as described above, or pharmaceutically acceptable salts thereof, in combination with a pharmaceutically acceptable carrier. Pharmaceutical compositions adapted for oral, topical or parenteral administration, comprising an amount of RhoB or RhoB variant constitute a preferred embodiment of the invention. The dose administered to a patient, particularly a human, in the context of the present invention should be sufficient to effect a therapeutic response in the patient over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to effect the desired response. The preferred dosage is the amount which results in maximum inhibition of cancer cell growth, without unmanageable side effects. Administration of RhoB protein (or a variant thereof) or a nucleic acid sequence encoding RhoB protein (or a variant thereof) can be continuous or at distinct intervals, as can be determined by a person of ordinary skill in the art.

Mammalian species which benefit from the disclosed methods for the inhibition of cancer cell growth, malignant cell transformation, and oncogenic signaling, include, but are not limited to, primates, such as apes, chimpanzees, orangutans, humans, monkeys; domesticated animals (e.g., pets) such as dogs, cats, guinea pigs, hamsters, Vietnamese potbellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. As used herein, the term "patient" is intended to include such human and non-human mammalian species. Likewise, in vitro methods of the present invention can be carried out on cells of such mammalian species.

Patients in need of treatment using the methods of the present invention can be identified using standard techniques known to those in the medical profession.

As used herein, the terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, liver cancer, e.g., hepatic carcinoma, bladder cancer, colorectal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer;

stomach cancer; testicular cancer; uterine cancer; cancer of the urinary system, as well as other carcinomas and sarcomas.

As used herein, the term "metastasis" refers to the process by which cancer cells are spread to distant parts of the body, such as from one organ and/or tissue to another not directly connected with it. The term is also used herein to refer to a tumor that develops through the metastatic process. Thus, as used herein, the term "metastasis" refers to neoplastic cell growth (e.g., tumor cell growth) in an unregulated fashion and spread to distal tissues and organs of the body. As used herein, the phrase "inhibiting metastasis" refers to slowing and/or preventing metastasis or the spread of neoplastic cells to a site remote from the primary growth area.

As used herein, the term "invasion" refers to the spread of cancer cells to surrounding tissues. As used herein, the phrase "inhibiting invasion" refers to slowing and/or preventing the spread of cancer cells to surrounding tissues.

As used herein, the term "migration" refers to movement of cancer cells in vivo or in vitro. As used herein, the phrase "inhibiting migration" refers to slowing and/or preventing movement of cancer cells in vivo or in vitro.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

As used herein, the terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "(therapeutically) effective amount" refers to an amount of an agent (e.g., a drug) effective to treat a disease or disorder in a mammal. In the case of cancer, the therapeutically effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" refers to an amount which inhibits growth of a target cell, such as a tumor cell, either in vitro or in vivo, irrespective of the mechanism by which cell growth is inhibited. In a preferred embodiment, the growth inhibitory amount inhibits growth of the target cell in cell culture by greater than about 20%, preferably greater than about 50%, most preferably greater than about 75% (e.g. from about 75% to about 100%).

The terms "cell" and "cells" are used interchangeably herein and are intended to include either a single cell or a plurality of cells unless otherwise specified.

As used herein, the term "anti-cancer agent" refers to a substance or treatment that inhibits the function of cancer cells, inhibits their formation, and/or causes their destruction in vitro or in vivo. Examples include, but are not limited to, cytotoxic agents (e.g., 5-fluorouracil, TAXOL) and anti-signaling agents (e.g., the PI3K inhibitor LY).

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston), and anti-androgens such as flutamide, nilutamide, bicalutamide, leuprolide, and goserelin, etc.

As used herein, the term "anti-signaling agent" refers to agents that interfere with cancer cell malignancy by inhibiting specific aberrant signal transduction circuits in the cell in vitro and/or in vivo. The PI3K inhibitor LY is an example of an anti-signalling agent.

Following are examples that illustrate materials, methods, and procedures for practicing the invention. The examples are illustrative and should not be construed as limiting.

MATERIAL AND METHODS

Cell Culture, Antibodies and Reagents. NIH3T3 cells were maintained in Dulbecco's Minimum Essential Medium (DMEM) supplemented with 5% calf serum and 100 μg/ml of penicillin/streptomycin. NIH3T3 cells stably transfected with constitutively active H-Ras61L (H-Ras/3T3) were cultured in DMEM complete medium containing 400 μg/ml of geneticin. Human A-549, PANC-1, PC3, and C33A cell lines were obtained from ATCC and cultured in DMEM supplemented with 10% fetal bovine serum (FBS) and penicillin/ streptomycin. B16-F10 mouse melanoma cells were cultured in RPMI1640 supplemented with 10% FBS and penicillin/streptomycin.

Antibodies to RhoB and RhoA were purchased from SANTA CRUZ Inc., Santa Cruz, Calif. Rabbit anti-phospho-AKT ($Ser^{473}$) and AKT were purchased from Cell Signaling Technology, Inc., Beverly, Mass. LY294002, PD98059 and SB203580 were purchased from CALBIOCHEM, La Jolla, Calif.

Gene Constructs and RhoB Promoter Transcriptional Activity Assay. Constitutively active H-Ras61L, K-RasV12, N-RasV12, and dominant negative N17-H-Ras were kind gifts from Dr. Channing Der (University of North Carolina) (Khosravi-Far, R. et al, *Mol Cell Biol,* 1995, 15:6443–53; Quilliam, L. A. et al., *Mol Cell Biol,* 1994, 14:1113–21). Wild-type RhoA and RhoB were subcloned into hemagglutinin (HA)-tagged pcDNA3 (INVITROGEN). The orientation and the sequences of these genes were confirmed by DNA sequencing facilities at the H. Lee Moffitt Cancer Center, Tampa, Fla. RhoB promoter construct pGEI was kindly provided by Dr Y. Monden (Banyu Tsukuba Research, Japan) (Nakamura et al., 1996). pCMV-β-galactosidase vector was purchased from INVITROGEN. The plasmid containing CA-, DN-PI3K, Mek and Akt were kindly provided by Dr. Julie Y. Djeu (H. Lee Moffitt Cancer and Research Institute, Tampa, Fla.) (Jiang, K. et al., *Blood,* 2003, 101:236–44). β-galactosidase activity and luciferase assay kits were purchased from PROMEGA Corporation, Madison, Wis. The serum response element (SRE) reporter was provided by Dr. Richard Jove, H. Lee Moffitt Cancer and Research Institute, Tampa, Fla. (Turkson, J. et al., *Mol Cell Biol,* 1999, 19:7519–28). The serum response element (SRE) reporter construct and v-Src cDNA construct were kindly provided by Dr. Richard Jove, Oncology program, H. Lee Moffitt Cancer and Research Institute, Tampa, Fla. (Turkson, J. et al., *Mol Cell Biol,* 1999, 19:7519–28). Human EGFR, ErbB2 cDNA construct were kindly provided by Dr. Noreen Luetteke, H. Lee Moffitt Cancer and Research Institute, Tampa, Fla. (Luetteke, N. C. et al., *Genes Dev,* 1994, 8:399–413).

DNA transfection was performed with the standard lipofectamine protocol (INVITROGEN). Briefly, cells were plated in 60-mm plates, pGEI plasmid was used at 2 μg per plate, whereas all the other plasmids were used at 0.1–1.0 μg per plate. After transfection the cells were grown for another 36–48 h. Cells were then washed twice with PBS and lyzed in Promega Passive Lysis Buffer. Aliquots of the lysates were then used to measure the luciferase and β-galactosidase activities. The luciferase values were first divided by β-galactosidase values. The RhoB promoter transcriptional activity was determined by dividing the luciferase/β-Gal values from oncogene-transfected cells by those from pcDNA3-transfected cells. Renilla luciferase was used as a positive control for determining Ras and v-Src SRE activity in the same transfected cells. All the samples were performed in triplicate and the averages of 3 independent experiments were reported here.

Focus Formation Assay. NIH3T3 cells were seeded into 60-mm plates ($1\times10^6$ cell/per plate) one day prior to gene transfection. Cells were transfected with 0.1 μg of each Ras, EGFR, ErbB2, or v-Src expression vectors plus 0.9 μg of RhoA, RhoB cDNA or pcDNA3 vector control with lipofectamine (INVITROGEN) according to manufacturer's recommendation. Two days after transfection, the cells were seeded into 60-mm plates at a density of $2.5\times10^3$/per plate, and maintained in DMEM medium containing 1.5% CBS. The medium was changed every 3 days. 3–4 weeks later the cells were washed once with PBS and once with PBS/methanol (1:1), then washed with fresh anhydrous methanol and covered with crystal violet stain for 1 min at room temperature. Finally, the stain was displaced with water. The focus formation assay for A-549 cells was similarly performed as above except that following the transfection the cells were cultured in DMEM complete medium containing 400 μg/ml of geneticin (G418, MEDIATECH, Inc.). 3 weeks later, the cells were fixed with anhydrous methanol and stained with crystal violet; the plates were photographed. All the samples were performed in triplicate and a representative of 3 independent experiments was reported in the figure(s) and averages±standard deviation reported in the table.

Anchorage-independent Growth Assay. NIH3T3 cells were similarly transfected as above. The cells were trypsinized, and $2.5\times10^3$ cells were suspended in triplicate in top soft agar layer (DMEM complete medium containing 0.35% agar) and seeded into 60-mm plates pre-coated by a 3-mm layer of lower agar (DMEM complete medium containing 0.7% agar). The cells were fed every 5 days for 5–6 weeks and finally stained with MTT (SIGMA). All the experiments were performed in triplicate and a representative of 3 independent experiments was reported in the figure(s) and averages±standard deviation in the table.

Western Blot Analysis. Whole cell lysates were prepared in a lysis buffer containing 20 mM Tris-HCl (pH 7.5), 150 mM NaCl, 1% NP-40, 1 mM phenylmethylsulfonyl fluoride, 1.5 μg each of aprotinin and leupeptin per ml, 10 mM NaF, 10 mM $NaPP_i$, 3 mM sodium vanadate, and 15 mM lycerolphosphate. Lysates were incubated 30 min on ice and centrifuged at 13,000×g for 10 min at 4° C. prior to SDS-PAGE and Western blotting. 50 μg of lysates was loaded for each sample. Antigen-bound antibody was detected by enhanced chemiluminescence Western blotting kit (AMERSHAM PHARMACIA BIOTECH), Piscataway, N.J.). β-actin was detected as an internal loading control.

Cell Proliferation. Cells were collected and examined for cell number by trypan blue exclusion and hemocytometer counting under microscope at 0 h, 24 h, 48 h, 72 h and 96 h. All the samples were performed in triplicate and the averages of 3 independent experiments were reported.

Apoptosis Assay. Cells were collected by trypsinization, washed in wash buffer and stained with Annexin V and 7-AAD according to manufacturer's recommendation (PharMingen, San Diego, Calif.). Data acquisition and analysis was performed by the Flow Cytometry Core Facility at the H. Lee Moffitt Cancer Center (Tampa, Fla.). All the samples were performed in duplicate and a representative of 3 independent experiments were reported here.

Anoikis Assay. Cells were collected by trypsinization, washed twice with PBS, and re-suspended in serum-free medium containing 0.5% BSA; $5.0\times10^5$ cells were then seeded in triplicates into 60-mm plates pre-coated with poly(2-hydroxyethylmethacrylate) (poly-HEMA, SIGMA) according to the data sheet of the agents. 24 hrs later the cellular viability was determined by trypan blue exclusion.

Melanoma Metastasis Assay. pcDNA3, pcDNA-RhoB and pcDNA-RhoA were transfected into B16-F10 cells similarly as described above. The cells were harvested 20 hours post-transfection; $5\times10^5$ cells from each group were analyzed for transfection efficiency by Western Blotting; another $5\times10^5$ cells were injected into the tail veins of C57/B16 mice (6 wk, F). The mice were sacrificed at the indicated intervals and the nodules growing in the lungs were counted.

EXAMPLE 1

Oncogenic H-Ras, N-Ras and K-Ras, EGFR, and ErbB2, but not v-Src, suppress RhoB promoter transcriptional activity in NIH3T3 cells and human cancer cell lines.

Proteins that induce malignant transformation and those that suppress tumorigenesis most likely antagonize each other's functions. Recent evidence points to a tumor suppressive function of the low molecular weight GTPase RhoB (Chen, Z. et al., *J Biol Chem,* 2000, 275:17974–8; Du, W. et al., *Mol Cell Biol,* 1999, 19:1831–40; Du, W. and Prendergast, G. C., *Cancer Res,* 1999, 59:5492–6). An objective of the experiments described herein was to determine whether oncogenes that are prevalent in human cancers suppress RhoB expression, and whether RhoB antagonizes the ability of these oncogenes to induce malignant transformation. To this end, the effects of several oncogenes on RhoB promoter transcriptional activity were first evaluated. NIH3T3 cells and human cancer cell lines derived from lung (A-549), pancreatic (Panc-1) and cervical (C33A) tumors were transiently transfected with pcDNA3 empty vectors or pcDNA3 constructs containing various oncogenes along with full length RhoB promoter firefly luciferase reporter and SRE-renilla luciferase reporter as well as a β-gal reporter for controlling transfection efficiency as described in the Materials and Methods section.

FIG. 1A–1J show that oncogenic H-, N- and K-Ras, EGFR, and ErbB2 inhibited RhoB promoter transcriptional activity in a dose-dependent manner in NIH3T3 cells. In contrast, v-Src had little effect on RhoB promoter activity (FIGS. 1F and 1H). As expected, v-Src did increase SRE promoter activity demonstrating that it is functional in these cells (FIGS. 1F and 1H). Furthermore, this v-Src increase of SRE promoter activity was similar to the increases seen with other oncogenes such as H-, N- and K-Ras as well as EGFR and ErbB2 (FIGS. 1A–1E, and 1G). Furthermore, EGFR inhibited RhoB promoter as early as 12 hrs after transfection whereas v-Src had little effect at all time points studied (FIGS. 1G and 1H). The effects of the oncogenes on RhoB promoter activity were also determined in human cancer cell lines. Table 1 shows that as in NIH3T3 cells (FIGS. 1A–1J), all Ras isoforms, EGFR, and ErbB2 but not v-Src, inhibit RhoB promoter activity in A-549, Panc-1 and C33A cells. Transfection of 1 μg constructs resulted in inhibition values that ranged from 60 to 80% (Table 1).

TABLE 1

Oncogenic H-, K-, N-Ras, EGFR and ErbB2, but not v-Src inhibit RhoB Promoter transcriptional activity (% inhibition)

| Cell line | Genes transfected | | | | | | |
|---|---|---|---|---|---|---|---|
| | pcDNA3 | H-Ras | K-Ras | N-Ras | EGFR | ErbB2 | v-Src |
| NIH3T3 | 0 | 76 ± 3.5 | 81 ± 4.8 | 77 ± 3.6 | 71 ± 5.7 | 79 ± 3.9 | 5.1 ± 9.3 |
| A549 | 0 | 73 ± 4.0 | 68 ± 4.9 | 69 ± 4.4 | 64 ± 6.1 | 74 ± 4.3 | 6.7 ± 8.8 |
| PANC1 | 0 | 64 ± 4.7 | 61 ± 6.3 | 73 ± 4.9 | 61 ± 6.8 | 68 ± 4.1 | 2.8 ± 12.1 |
| C33A | 0 | 70 ± 5.3 | 68 ± 3.8 | 64 ± 6.8 | 66 ± 5.5 | 69 ± 3.6 | −15 ± 13.2 |

NIH3T3, A549, PANC1, and C33A cell lines were transiently transfected with the indicated oncogenes or pcDNA3 vector control along with RhoB promoter reporter gene for 36 hrs. The cells were then processed as described under Methods for determination of the activation of RhoB promoter. The RhoB reporter activity in oncogene-transfected cells was reported here as the percentage of inhibition over pcDNA3 control-transfected cells.

EXAMPLE 2

The ability of EGFR and ErbB2 to suppress RhoB promoter transcriptional activity requires Ras.

The receptor tyrosine kinases EGFR and ErbB2 are known to activate Ras signaling (Alimandi, M. et al., *Oncogene,* 1995, 10:1813–21; Buday, L. and Downward, J., *Cell,* 1993, 73:611–20; Hunter, T., *Cell,* 1997, 88, 333–46). We, therefore, determined whether EGFR and ErbB2 require Ras for their ability to suppress RhoB promoter activity. To this end, NIH3T3 cells were transiently transfected with EGFR or ErbB2 along with RhoB promoter and SRE luciferase reporters as in FIGS. 1I and 1J. Dominant negative N17-H-Ras or empty vector pcDNA3 constructs were also transfected as described in the Materials and Methods section. FIGS. 1I and 1J show that transfection with 1 μg EGFR-pcDNA3 and 1 μg ErbB2-pcDNA3 in the absence of N17-H-Ras (DN-Ras) inhibited RhoB promoter activity by 71% and 80% respectively. However, in the presence of N17-H-Ras, EGFR and ErbB2 inhibited only slightly (22% and 18% respectively) (FIGS. 1I and 1J). As a control, it was also shown that EGFR and ErbB2 induced SRE promoter activity by 4.6 and 5.0 folds and that N17-H-Ras inhibited EGFR and ErbB2 from inducing SRE promoter activity (FIG. 1J). Thus, the ability of EGFR and ErbB2 to suppress RhoB promoter activity was hampered by dominant negative N17-H-Ras suggesting that Ras mediates EGFR and ErbB2 suppression of RhoB expression.

EXAMPLE 3

The ability of the anticancer drug 5-FU to Induce RhoB promoter activity is inhibited by H-, N-, and K-Ras oncogenes The results shown in FIGS. 1A–1J demonstrate that certain oncogenes suppress basal (unstimulated) RhoB promoter activity. Because RhoB is usually expressed at low levels and that its gene is inducible by physical (γ-irradiation, UV) and chemical (DMS, N-methyl-N-nitrosourea, $H_2O_2$, cisplatin, TAXOL) agents (Fritz, G. and Kaina, B., *J Biol Chem,* 1997, 272:30637–44; Fritz, G. et al., *J Biol Chem,* 1995, 270:25172–7), it would be important to determine whether oncogenes also suppress inducible RhoB levels. To this end, NIH3T3 cells were transiently transfected with oncogenes along with RhoB promoter and SRE luciferase reporter constructs as described for the experiments of FIGS. 1A–1J. The cells were then treated 24 hours later with either DMSO vehicle or 5-FU (2 μM) for 12 hours as described in the Materials and Methods section. FIG. 2A shows that treatment of cells with 5-FU, in the absence of oncogenes, induced RhoB promoter activity by more than 4-fold whereas transient transfection with H-, N- and K-Ras in the absence of 5-FU suppressed RhoB promoter activity by 73%, 79%, and 78%, respectively. In contrast, in the presence of H-Ras, N-Ras, and K-Ras, 5-FU induced RhoB promoter activity by only one fold or less than one fold (FIG. 2A). Thus, the ability of 5-FU to induce RhoB promoter activity was potently inhibited by oncogenes.

EXAMPLE 4

H-Ras, N-Ras, and K-Ras suppress the protein levels of RhoB

Figure 2B:
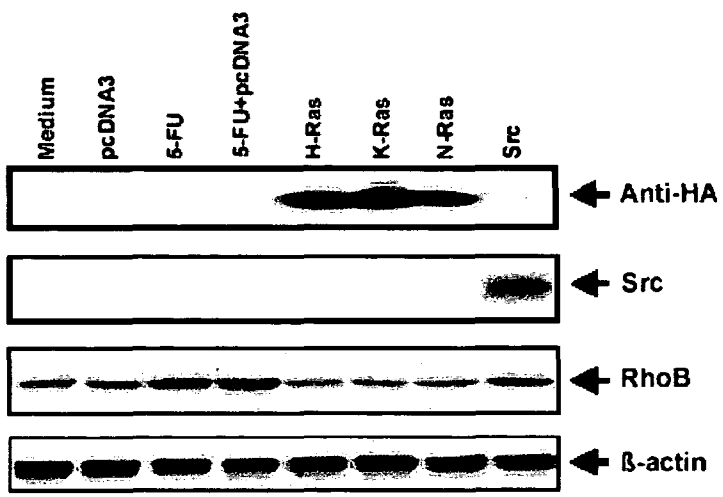

FIGS. 1A–1J and FIG. 2A demonstrate that basal and induced RhoB promoter activities are suppressed by oncogenes. To determine whether RhoB protein levels are also affected by oncogenes, NIH3T3 cells were transiently transfected with HA-tagged oncogenes and determined their effects on basal endogenous levels of RhoB. FIG. 2B shows that non-transfected cells (medium) or cells transfected with empty pcDNA3 vector contained no HA-tagged proteins and express low but detectable levels of RhoB. Transfection with oncogenic Ras and v-Src genes resulted in their expression, as documented by anti-HA and anti-Src immunoblotting, respectively (FIG. 2B). Transfection with Ras, but not v-Src, resulted in the suppression of RhoB protein levels (FIG. 2B). To document that RhoB protein levels are inducible, NIH3T3 cells were treated with the anticancer drug 5-FU in the absence of oncogenes and showed that RhoB was indeed induced by this agent (FIG. 2B).

EXAMPLE 5

Induction of RhoB protein levels by 5-FU is blocked by H-, N- and K-Ras

Figure 2C:
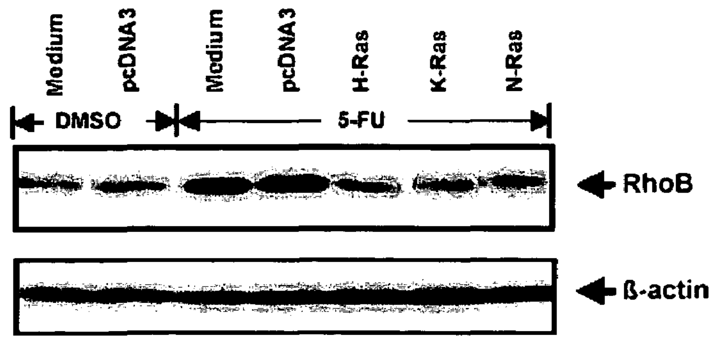

FIG. 2A shows that the ability of 5-FU to induce RhoB promoter activity is hampered by Ras oncogenes. Whether this also occurs at the protein level was evaluated next. FIG. 2C shows that treatment of NIH3T3 cells with 5-FU for 36 hrs induced RhoB protein levels by 3-fold. Ectopic expression of H-Ras, N-Ras, K-Ras blocked the ability of 5-FU to induce RhoB protein levels (FIG. 2C).

EXAMPLE 6

Ectopic expression of RhoB, not RhoA, potently inhibits H-, N- and K-Ras, EGFR, ErbB2 but not v-Src transformation in NIH3T3 cells.

Figure 3A:
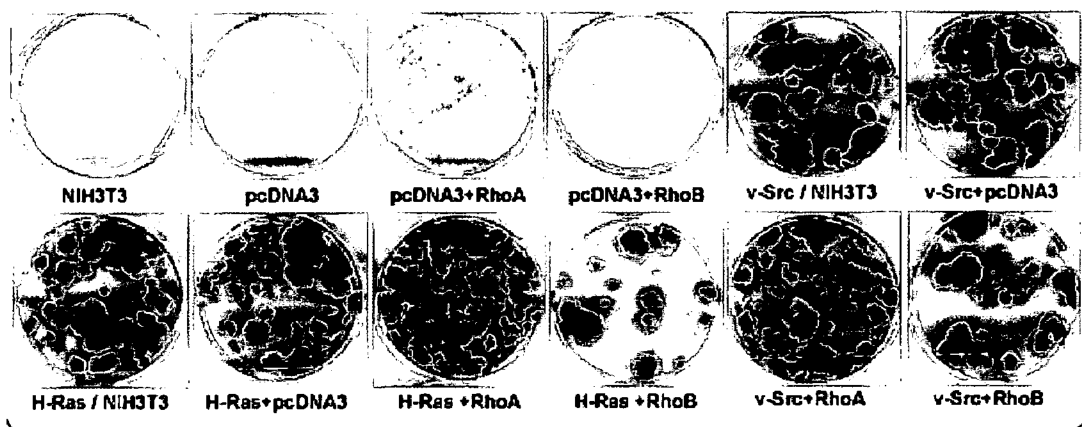
FIGS. 3A–3C show that the ability of Ras to transform NIH3T3 cells is inhibited by ectopic expression of RhoB, but not RhoA. NIH3T3 cells were transiently transfected with H-Ras or v-Src oncogene or pcDNA3 vector control in the presence or absence of RhoA or RhoB for 36 hrs. The cells were then trypsinized and cultured in DMEM medium containing 1.5% calf bovine serum for determination of their capability to form foci. 28 days later the foci were stained and photographed as described in the Materials and Methods section. Results are shown in FIG. 3A. RhoB, not RhoA, inhibits H-Ras-induced soft agar colony formation. NIH3T3 cells were similarly transfected as in FIG. 3A. The cells were then trypsinized and suspended in DMEM-soft agar for determination of their capability to form colonies. 5 weeks later the colonies were stained with MTT and scanned as described in the Materials and Methods section. Results are shown in FIG. 3B. Ectopic expression of RhoB, but not RhoA, inhibits focus formation of human lung cancer A-549 cells. A-549 cells were transiently transfected with pcDNA3 vector control, RhoA or RhoB for 36 hrs. The cells were cultured in G418-containing DMEM medium for determination of their capability to form foci, 21 days later the foci were fixed, stained with crystal violet and photographed as described in the Materials and Methods section. Results are shown in FIG. 3C.

The results described in 1A–1J and FIGS. 2A–2C demonstrate that RhoB promoter activity and RhoB protein basal and induced levels are suppressed by oncogenes. It was reasoned that if some oncogenes must suppress RhoB expression as one of the required steps in their mechanism by which they transform cells, then forced expression of RhoB should block transformation induced by such oncogenes. To this end, NIH3T3 cells were transfected with pcDNA3 constructs that carry H-, N- and K-Ras, EGFR, ErbB2 or v-Src in the presence or absence of pcDNA3 constructs that contain RhoB and followed transformation by focus formation and soft agar assays as described in the Materials and Methods section. As a control, similar experiments were also performed with RhoA, a closely related family member that shares 86% amino acid sequence identity with RhoB. FIG. 3A shows that parental NIH3T3 cells or pcDNA3 empty vector-transfected cells grew many foci when transformed by oncogenic H-Ras or v-Src. Transformation by H-Ras along with RhoA increased the number of foci formed, so did the transformation by v-Src along with RhoA (FIG. 3A). In contrast, transformation with H-Ras in the presence of RhoB resulted in much fewer foci (FIG. 3A). Table 2 shows that similar results were obtained with other forms of Ras (K- and N-Ras) as well as other oncogenes such as EGFR and ErbB2. In contrast, ectopic expression of RhoB affected much less the transforming ability of v-Src which did not suppress RhoB promoter activity (FIG. 3A and Tables 1 and 2). Indeed, quantitation of the results shows that RhoB inhibited focus formation by H-, N- and K-Ras, EGFR and ErbB2 by 62%, 39%, 61%, 56% and 59%, but inhibited v-Src transformation by only 15%.

TABLE 2

Oncogenic H-, K-, N-Ras, EGFR and ErbB2-induced transformation is suppressed by RhoB (# of foci formed)

| Genes co- | Oncogenes transfected | | | | | |
|---|---|---|---|---|---|---|
| transfected | H-Ras | K-Ras | N-Ras | EGFR | ErbB2 | v-Src |
| pcDNA3 | 47 ± 6 | 41 ± 6 | 36 ± 4 | 39 ± 5 | 46 ± 7 | 31 ± 3 |
| RhoA | 63 ± 11 | 71 ± 13 | 46 ± 8 | 47 ± 7 | 61 ± 11 | 35 ± 7 |
| RhoB | 18 ± 3 | 16 ± 4 | 22 ± 3 | 17 ± 3 | 19 ± 4 | 26 ± 6 |

NIH3T3 cells were transiently transfected with H-, K- and N-Ras, EGFR, ErbB2, or v-Src in the presence or absence of RhoA or RhoB or pcDNA3 vector control for 36 hrs. The cells were then cultured in DMEM containing 1.5% calf bovine serum for determination of their capability to form foci. 4 weeks later the plates were stained and scanned.

Figure 3B:
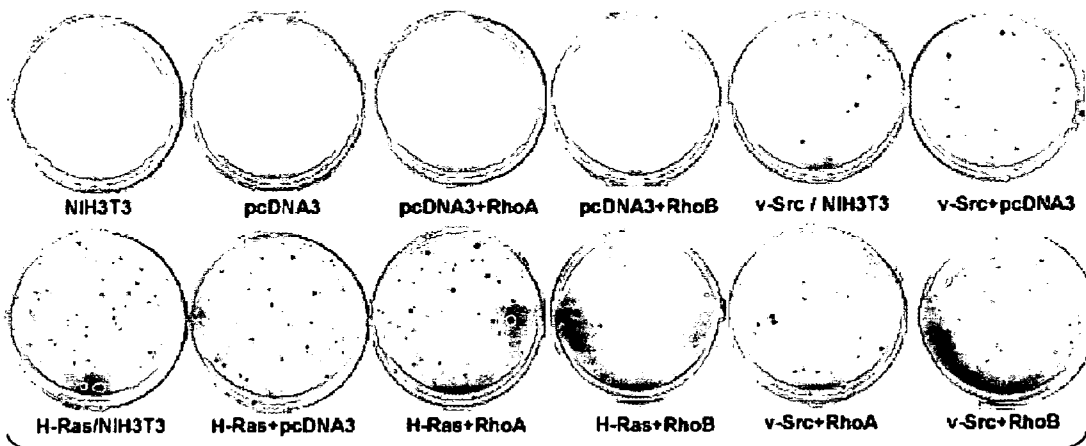

Next, the ability of RhoB to antagonize oncogene transformation was confirmed by soft agar assays. To this end, NIH3T3 cells were transfected with H-Ras, N-Ras, K-Ras or v-Src along with either empty pcDNA3 vector or pcDNA3 containing RhoB or RhoA and the cells plated on soft agar as described in the Materials and Methods section. FIG. 3B shows that parental NIH3T3 cells, or those transfected with either pcDNA3, RhoA or RhoB grew no colonies on soft agar. In contrast, H-Ras, N-Ras, K-Ras and v-Src-transfected cells grew many colonies (FIG. 3B and Table 3). While RhoA slightly enhanced, RhoB inhibited the ability of Ras, but not v-Src to transform NIH3T3 cells (FIG. 3B and Table 3). Table 3 shows that the number of colonies formed in H-, N- and K-Ras transformed NIH3T3 were 54, 63 and 42, respectively. In the presence of RhoA these numbers were 77, 89 and 65. In contrast, in the presence of RhoB the number of soft agar colonies were 21, 26 and 18, respectively.

TABLE 3

Oncogenic H-, K-, N-Ras-induced transformation is suppressed by RhoB (# of soft agar colonies)

| | Oncogenes | | |
|---|---|---|---|
| | H-Ras | K-Ras | N-Ras |
| pcDNA3 | 54 ± 7 | 42 ± 8 | 63 ± 10 |
| RhoA | 77 ± 12 | 65 ± 7 | 89 ± 14 |
| RhoB | 21 ± 3 | 18 ± 5 | 26 ± 7 |

NIH3T3 cells were transiently transfected with the indicated oncogenes or pcDNA3 vector control in the presence or absence of RhoA or RhoB for 36 hrs. The cells were then trypsinized and suspended in DMEM-soft agar for determination of their capability to form colonies. 5 weeks later the colonies were stained with MTT and scanned.

EXAMPLE 7

Ectopic expression of RhoB, but not RhoA, inhibits colony formation of human lung cancer A-549 cells.

Figure 3C:
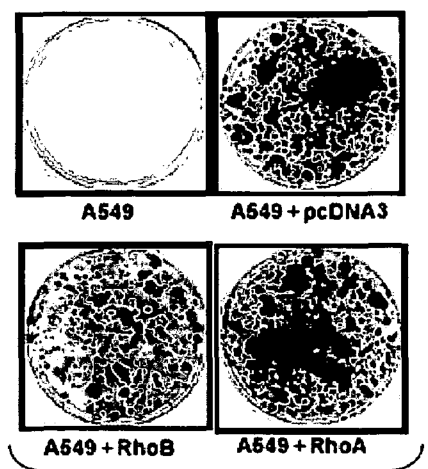

FIGS. 3A and 3B and Tables 2 and 3 show that forced expression of RhoB antagonizes the ability of Ras oncogenes to transform NIH3T3 cells. Whether RhoB could antagonize the ability of A-549 cells (which naturally express a mutant K-Ras) to form colonies was determined next. To this end, A-549 cells were transfected with either pcDNA3 empty vector, RhoA- or RhoB-containing pcDNA3 constructs and cultured in media containing G418 and colonies detected 3 weeks later as described in the Materials and Methods section. FIG. 3C shows that parental A-549, which did not receive pcDNA3, were sensitive to G418 and did not grow. In contrast, A-549 transfected with pcDNA3 grew numerous colonies. Furthermore, expression of RhoA did not hamper the ability of A-549 cells to grow colonies. However, expression of RhoB resulted in inhibition of A-549 colony formation (FIG. 3C). The actual number of colonies from pcDNA3-, RhoA- and RhoB-transfected A-549 cells were 417+/−21, 593+/−43 and 178+/−19, respectively.

EXAMPLE 8

Ectopic expression of RhoB inhibits the proliferation of A-549 cells, oncogenic H-Ras-transformed NIH3T3 cells but not non-transformed NIH3T3 cells.

Figure 4A:
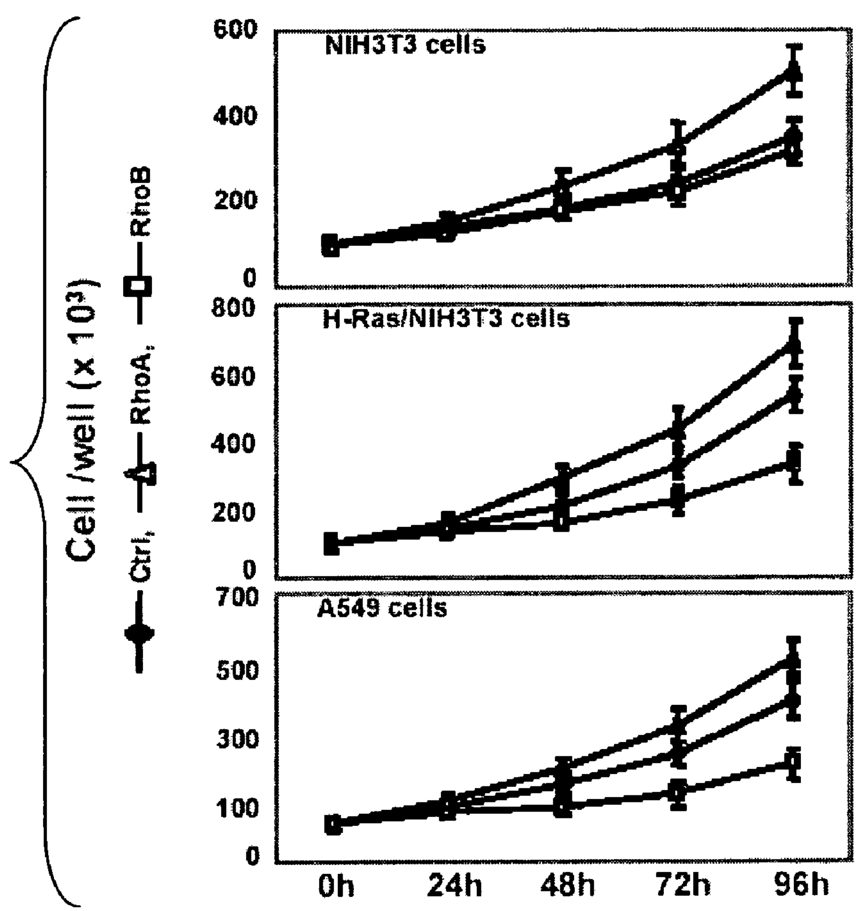
FIGS. 4A–4C show that RhoB inhibits the proliferation of A-549 cells and H-Ras transformed, but not parental NIH3T3 cells, whereas RhoA enhances the proliferation of all 3 cell lines. Parental NIH3T3, NIH3T3 cells transformed by constitutively active H-Ras61L (H-Ras/NIH3T3), and A549 human lung cancer cells were transiently transfected with pcDNA3 vector control, RhoA, or RhoB for 36 hrs. The cells were then cultured in DMEM medium and counted for cell number at the time points indicated for determination of their ability to proliferate as described in the Materials and Methods section. Results are shown in FIG. 4A. RhoB, but not RhoA, reverses H-Ras-mediated resistance to 5-FU-induced apoptosis. Parental NIH3T3 and H-Ras/NIH3T3 were transiently transfected with pcDNA3 vector control, RhoA, or RhoB for 24 hrs. The cells were then cultured in DMEM medium containing DMSO or 2.0 μM 5-FU for another 48 hrs. Next, the cells were examined for their susceptibility to 5-FU-induced apoptosis by Annexin V labeling and flow cytometry apoptosis assays as described in the Materials and Methods section. Results are shown in FIG. 4B. RhoB, not RhoA, induces anoikis in A-549 and H-Ras/NIH 3T3 cells. A-549 and H-Ras/NIH3T3 cells were similarly transfected as above (without 5-FU treatment), collected and re-suspended in serum-free medium containing 0.5% BSA; $1.0\times10^5$ cells were then seeded in triplicate into 12-well plates pre-coated with poly-HEMA. Cellular viability was checked by trypan blue exclusion at the time points indicated. Cellular viability is shown in FIG. 4C.

The ability of RhoB to interfere with the cell growth of non-transformed NIH3T3 fibroblasts, H-Ras-transformed NIH3T3 fibroblasts, and the human lung cancer cell line A549 was evaluated. Cells were transfected with pcDNA3 empty vector, RhoA or RhoB-containing pcDNA3 as described for the experiments shown in FIGS. 3A–3C, and cell numbers counted at 0, 24, 48, 72 and 96 hours as described in the Materials and Methods section. FIG. 4A shows that RhoA enhanced the rate of growth of all 3 cell lines. In contrast, RhoB inhibited the growth rate of A-549 cells and H-Ras-transformed NIH3T3 cells (FIG. 4A). Interestingly, the growth rate of non-transformed NIH3T3 cells was not affected by RhoB (FIG. 4A).

EXAMPLE 9

Oncogenic H-Ras-mediated resistance to 5-FU-induced apoptosis is reversed by RhoB.

Figure 4B:
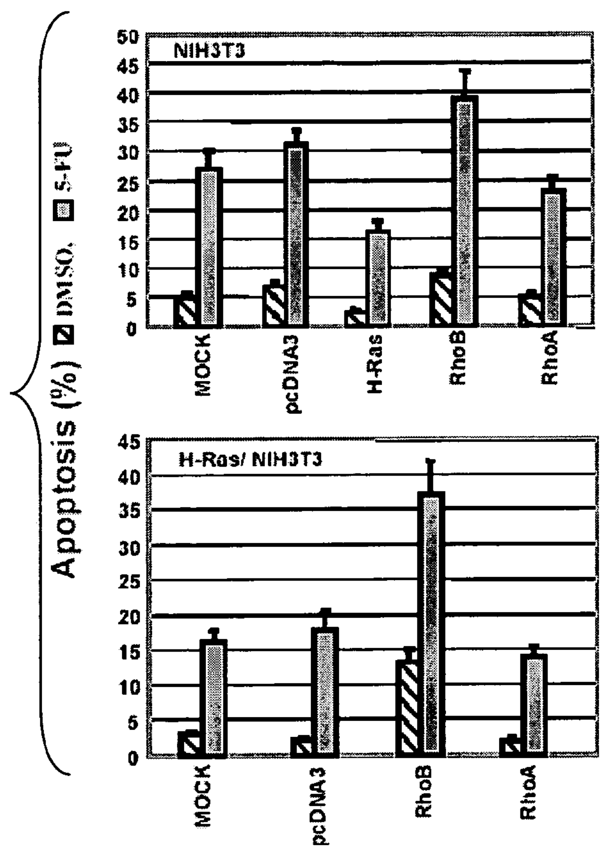

Since 5-FU induces RhoB promoter activity and protein levels, whether RhoB also enhances the ability of 5-FU to induce apoptosis was determined. Furthermore, whether RhoB could reverse Ras-mediated resistance to 5-FU apoptosis was also determined. NIH3T3 cells or oncogenic H-Ras-transformed NIH3T3 cells were transiently transfected with pcDNA3 empty vector, H-Ras, RhoA or RhoB for 24 hours and treated with DMSO vehicle or 5-FU for an additional 48 hours and apoptosis analyzed by Annexin V labeling and flow cytometry as described in the Materials and Methods section. FIG. 4B shows that 5-FU induced 27–32% apoptosis in parental NIH3T3 cells and only 16–18% apoptosis in H-Ras-transformed NIH3T3 cells. Transfection with H-Ras in NIH3T3 cells partially inhibited the ability of 5-FU to induce apoptosis. RhoA had no significant effect on 5-FU-induced apoptosis. In contrast, RhoB enhanced the ability of 5-FU to induce apoptosis in both cell lines (FIG. 4B). The effect was more prominent in H-Ras-transformed cells where RhoB increased the percent of apoptosis from 16% to 37% whereas in the parental cells it increased the percent of apoptosis from 28% to 39%.

EXAMPLE 10

RhoB, but not RhoA, induced anoikis

Figure 4C:
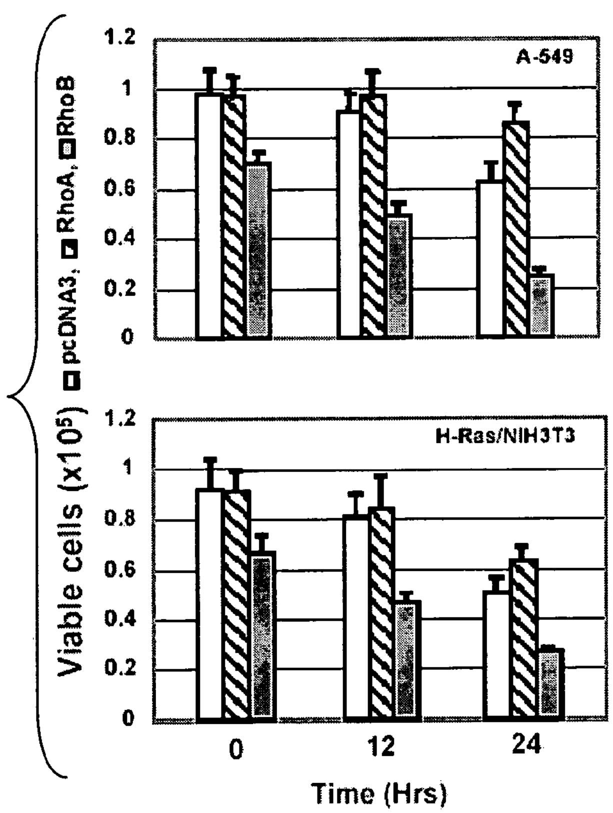

Whether RhoB can induce anoikis in H-Ras-transformed NIH3T3 cells and A-549 cells was determined. Transformed cells, but not non-transformed cells, continue to survive when deprived from substratum attachment. Therefore, the H-Ras-transformed NIH3T3 cells and A-549 cells were transfected with either pcDNA3, RhoA or RhoB constructs for 36 hrs, and trypsinized, counted and seeded these cells onto poly-HEMA coated plates for 0, 12 and 24 hrs. Live cells were then counted as described in the Materials and Methods section. FIG. 4C shows that depriving A-549 cells from substratum attachment resulted in only 40% cell death over a 24 hr period. However, in the presence of RhoB, over the same period of time, 78% of A-549 cells died. Thus, RhoB enhanced anoikis in A-549 cells. In contrast, RhoA protected these cells from anoikis (FIG. 4C). Similarly, RhoA was slightly protected from anoikis, whereas RhoB enhanced anoikis, in H-Ras-transformed NIH3T3 cells (FIG. 4D).

EXAMPLE 11

Ras downregulation of RhoB promoter transcriptional activity is mediated by PI3K and Akt but not Mek1/2.

Figure 5A:
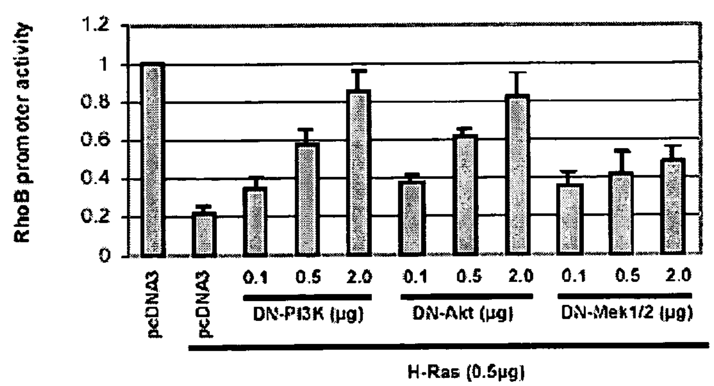
FIGS. 5A–5D show that oncogenic PI3K/Akt, but not Mek1/2, mediate Ras suppression of RhoB promoter transcriptional activity in NIH3T3 cells. NIH3T3 cells were transiently transfected with various oncogene constructs (H-Ras, DN-PI3K, DN-Akt1, DN-Mek1/2, CA-PI3K, CA-Akt1 and CA-Mek1/2) or pcDNA3 vector control along with full length RhoB promoter-firefly luciferase reporter and SRE-Renilla luciferase reporter for 36 hrs and the cell lysates were processed for determination of RhoB and SRE promoter activity as described in the Materials and Method section. The data are reported as ratios of Luci/β-gal from the cells transfected by the oncogene(s) over those from pcDNA3 transfected cells.
Figure 5B:
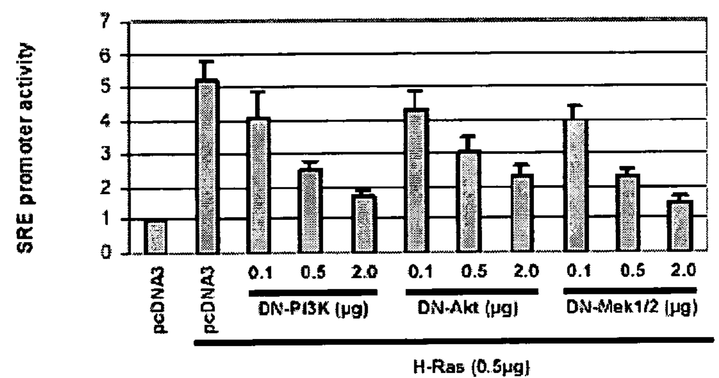
Figure 5C:
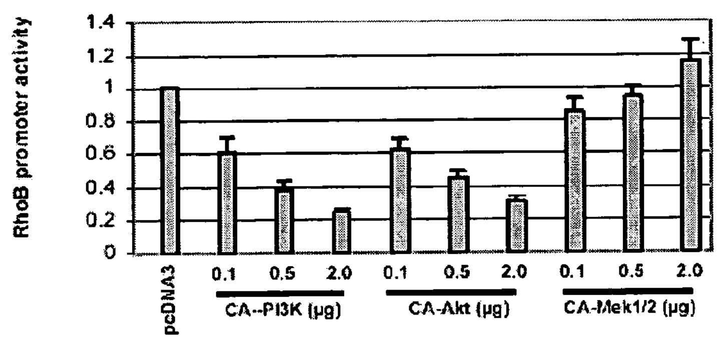
Figure 5D:
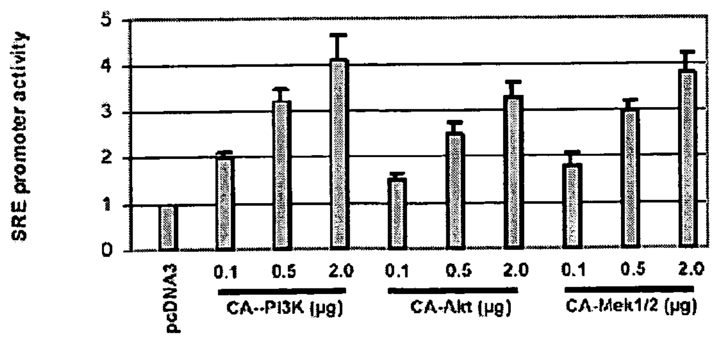

The fact that RhoB has tumor suppressive activity (Chen, Z. et al., *J Biol Chem,* 2000, 275:17974–8; Du, W. and Prendergast, G. C. *Cancer Res,* 1999, 59:5492–6; Du, W. et al., *Mol Cell Biol,* 1999, 19:1831–40) and that RhoB levels decrease dramatically with the aggressiveness of tumors (Adnane, J. et al., *Clin Cancer Res,* 2002, 8:2225–32; Forget, M. A. et al., *Clin Exp Metastasis,* 2002, 19:9–15) prompted the present inventor to test the hypothesis that oncogenic and tumor survival pathways downregulate RhoB as a step leading to malignant transformation. The present inventor has shown that EGFR, ErbB2, and Ras, but not Src, inhibits RhoB expression. Here, the present inventor investigated the role of the PI3K/Akt and Mek limbs of the Ras pathways in this RhoB downregulation. To this end, NIH3T3 cells were transfected with a RhoB promoter firefly luciferase reporter, SRE renilla reporter along with various DNA constructs as described in the Materials and Methods section. FIGS. 5A and 5B show that transfection with oncogenic HRas resulted in a 78% inhibition of RhoB promoter activity. This suppression of RhoB promoter activity was rescued in a concentration-dependent manner by dominant negative forms of PI3K (DN-PI3K) and Akt1 (DN-Akt), suggesting that PI3K and Akt1 are required for H-Ras to inhibit RhoB promoter activity. Similar results were obtained with dominant negative Akt2. FIGS. 5A and 5B also show that while DN-PI3K and DN-Akt inhibited the ability of Ras to suppress RhoB promoter activity by 79% and 76%, DN-Mek Akt1/2 was only able to inhibit by 30%. In contrast, the ability of Ras to induce SRE promoter activity was equally inhibited by DN-PI3K, DN-Akt and DN-Mek 1/2. Therefore, the Ras suppression of RhoB promoter activity is primarily mediated by the PI3K/Akt pathway. Consistent with this is the demonstration that constitutively activated CA-PI3K and CA-Akt, but not CA-Mek1/2, inhibited RhoB promoter activity (FIGS. 5C and 5D). Finally, the present inventor has also shown that the downregulation of RhoB by 2 receptor tyrosine kinases, EGFR and ErbB2 also requires PI3K and Akt but not Mek.

EXAMPLE 12

Activation of the Ras/PI3K/Akt pathway results in resistance to the induction of RhoB promoter activity by the anticancer drug 5-fluorouracil.

Figure 6A:
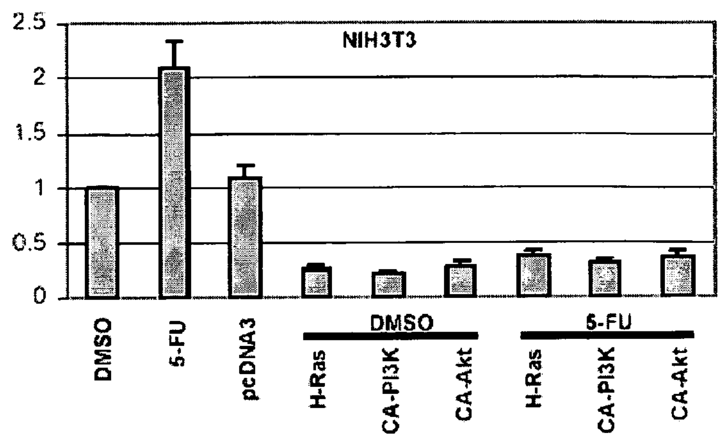
FIGS. 6A–6D show that the ability of 5-FU to induce RhoB promoter activity is antagonized by oncogenic Ras, PI3K and Akt in NIH3T3 cells.
Figure 6B:
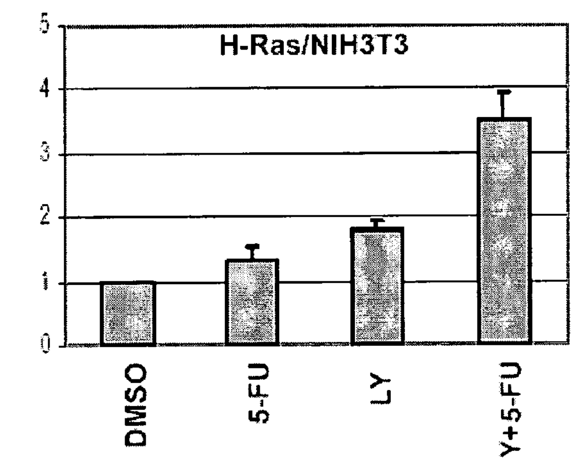
Figure 6C:
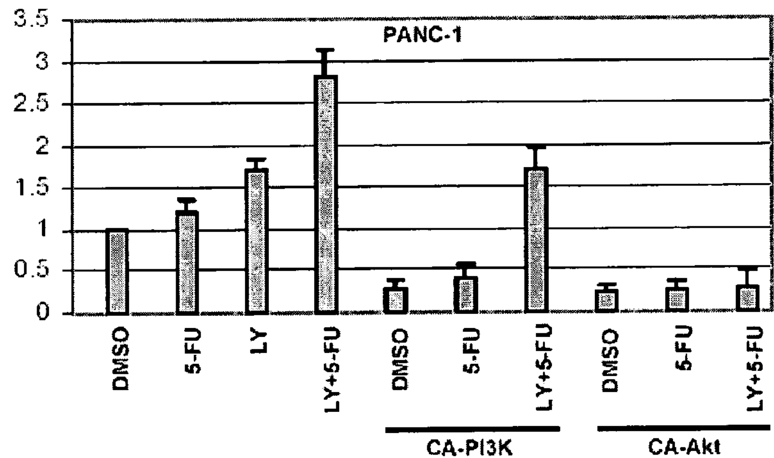
Figure 6D:
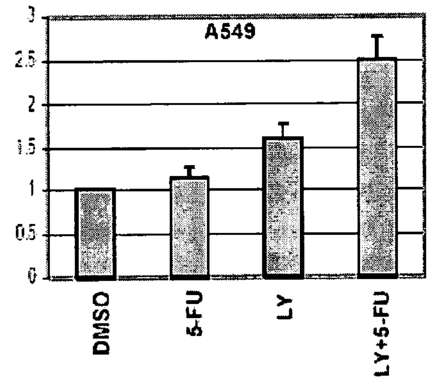

FIGS. 5A–5D demonstrated that the Ras/PI3K/Akt pathway inhibits the basal level (unstimulated) of RhoB promoter transcriptional activity. However, RhoB is usually expressed at very low levels but is induced by physical (UV and γ irradiation) and chemical (TAXOL, cisplatin, $H_2O_2$) agents (Fritz, G. et al., *J Biol Chem,* 1995, 270:25172–7; Fritz, G. and Kaina, B. *J Biol Chem,* 1997, 272:30637–44). Therefore, the present inventor next determined whether the Ras/PI3K/Akt pathway also suppresses the induction of RhoB. To this end, NIH3T3 cells were transfected with RhoB promoter reporter, SRE promoter reporter, and treated with either DMSO or the anticancer drug 5-fluorouracil (5-FU) as described in the Materials and Method section. FIG. 6A shows that treatment of NIH3T3 cells with 5-FU induced RhoB promoter activity by 2-fold, whereas transfection with oncogenic H-Ras, CA-PI3K, and CA-Akt inhibited RhoB promoter activity by 76%, 72% and 70%, respectively. Furthermore, in the presence of oncogenic H-Ras, CA-PI3K or CA-Akt, 5-FU was unable to stimulate RhoB promoter activity (FIG. 6A). Consistent with this, FIG. 6B shows that 5-FU had little effect on RhoB promoter activity in NIH3T3 cells that stably express oncogenic H-Ras. FIG. 6B shows that treatment of H-Ras/3T3 cells with LY294002, a pharmacological inhibitor of PI3K (Yano, H. et al., *Biochem J,* 1995, 312 (Pt 1):145–50; Vlahos, C. J. et al., *J Biol Chem,* 1994, 269:5241–8) alone induced RhoB promoter activity by 1.7-fold whereas treatment with both 5-FU and LY294002 induced it by 3.5-fold, suggesting that inhibition of PI3K sensitizes HRas/3T3 cells to 5-FU. Taken together, the data from FIGS. 6A and 6B demonstrate that the H-Ras/PI3K/Akt pathway down-regulates RhoB in NIH3T3 cells.

Figure 7A:
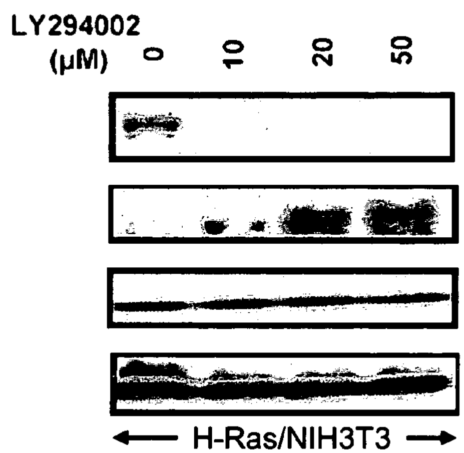
Figure 7B:
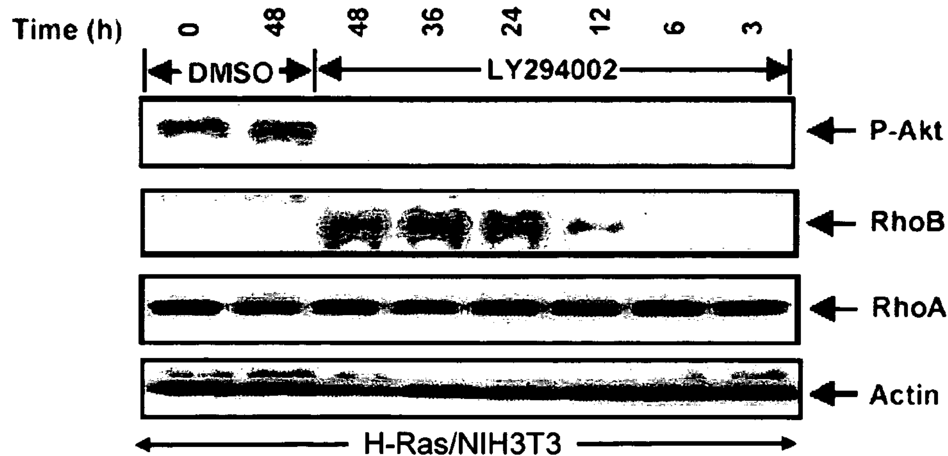
Figure 7C:
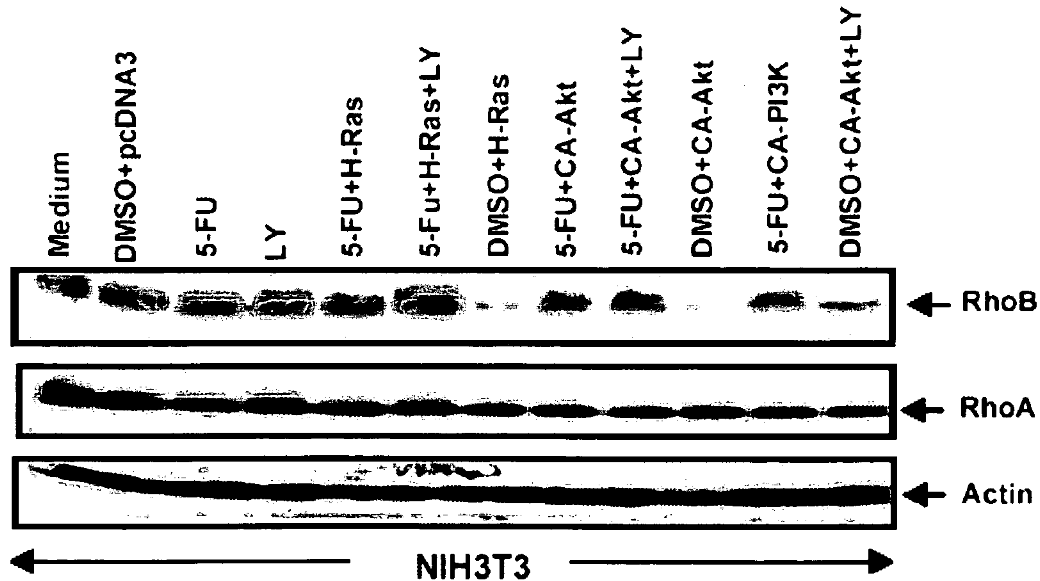

To determine whether this holds true for human cancer cells, the present inventor performed similar experiments in pancreatic (PANC-1) and lung (A-549) cancer cells both of which express mutated K-Ras. FIGS. 7C and 7D show that both cell lines are resistant to 5-FU and that treatment with LY294002 sensitize these cells to 5-FU induction of RhoB promoter activity. Furthermore, FIG. 7C also shows that transfection of PANC-1 cells with CAPI3K and CA-Akt inhibits both basal and 5-FU-induced RhoB promoter activity, and LY294002 reverses the CA-PI3K but not the CA-Akt suppression.

EXAMPLE 13

Blocking the H-Ras/PI3K/Akt pathway induces RhoB protein levels

FIGS. 5A–5D and 6A–6D demonstrate that the Ras/PI3K/Akt pathway downregulates RhoB promoter transcriptional activity. The relevance of this important finding to endogenous RhoB protein, was documented by showing that in the absence of LY294002, H-Ras/3T3 cells contained phosphorylated Akt (P-Akt) and expressed little RhoB, while treatment with LY294002 inhibited P-Akt levels and increased RhoB protein levels (FIG. 7A). In contrast, the levels of RhoA, a closely related family member, did not change following LY294002 treatment. FIG. 7B shows that the induction of RhoB protein levels was detectable as early as 12 hours after LY294002 treatment. Next, parental NIH3T3 cells were analyzed and it was found that 5-FU induces RhoB protein levels and that oncogenic HRas, CA-PI3K and CA-Akt all decreased both basal and 5-FU-induced RhoB protein levels (FIG. 7C). Treatment with LY294002 sensitizes oncogenic H-Ras-, but not CA-, Akt transfected cells to 5-FU induction of RhoB expression, consistent with H-Ras being upstream whereas Akt being downstream of PI3K, the target for LY294002. The relevance of these findings to human cancer cells was documented in FIGS. 7D–7F. FIG. 7D shows that dominant negative forms (DN) of Akt1 and Akt2 induced RhoB protein levels slightly when used alone, but the induction was greater when both DN-Akt1 and DN-Akt2 were co-transfected into PANC-1 cells. FIG. 7D also shows that transfection of PANC-1 cells with both DN-Akt1 and DN-Akt2 sensitized these cells to 5-FU induction of RhoB. FIG. 7E shows that treatment of PANC-1 cells with LY294002 induced RhoB, but not RhoA, protein levels by 8-fold. Treatment of PANC-1 cells with PD98059 (a Mek inhibitor) resulted in no induction. FIG. 7F shows that in another human cancer cell line, A549, LY294002 treatment similarly sensitized these cells to 5-FU induction of RhoB protein levels.

EXAMPLE 14

Figure 8A:
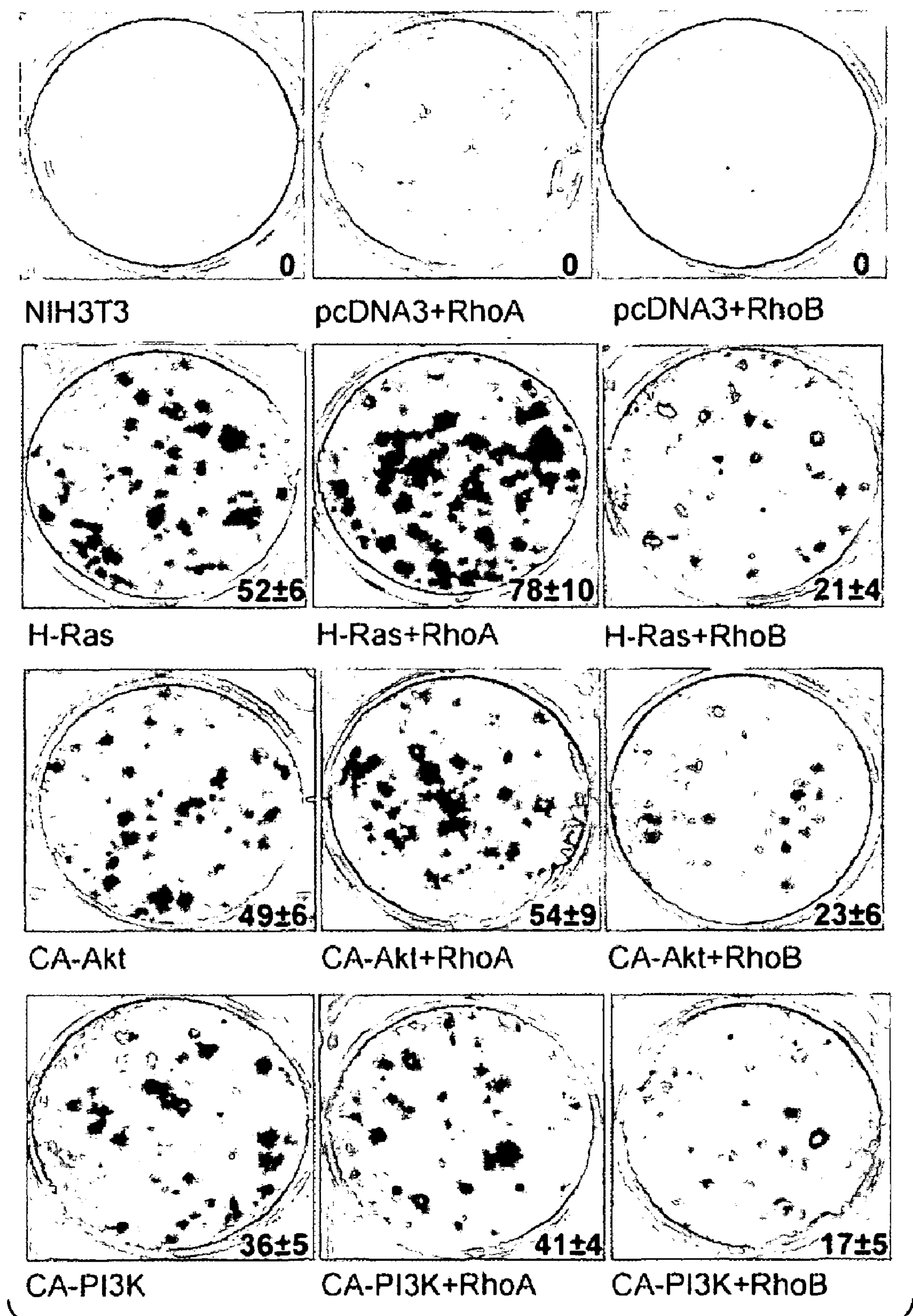
FIGS. 8A–8E demonstrate that ectopic expression of RhoB, not RhoA, inhibits Ras/PI3K/Akt-mediated transformation and migration. Parental NIH3T3 (FIG. 8A) were transiently transfected with pcDNA3 vector control, H-Ras61L, CA-PI3K, or CA-Akt in the presence or absence of RhoA or RhoB or pcDNA3 for 36 hours. The cells were then split and cultured for another 4 weeks. The plates were examined for focus formation by staining. H-Ras/3T3 cells (FIG. 8B) and PANC-1 cells (FIG. 8C) were transiently transfected with pcDNA3 vector control, CA-Akt, or WT-Akt in the presence or absence of RhoA, RhoB, or pcDNA3 for 36 hours. The cells were then split and analyzed for their migration capabilities through collagen type I coated trans-filters as described in the Materials and Methods section. NIH3T3 cells (FIGS. 8D and 8E) were transiently transfected with pcDNA3 vector control, H-Ras61L, CA-Akt, or WT-Akt in the presence or absence of RhoA, RhoB, or pcDNA3 for 36 hours. The monolayers were then scratched with a 20 μl pipette tip and micro-photographed at the time points indicated for analyzing their capability to migrate into and fill the wounded area.

The ability of oncogenic H-Ras, CA-PI3K and CA-Akt to transform NIH3T3 cells is antagonized by ectopic expression of RhoB, not RhoA FIGS. 5A–5D, 6A–6D, and 7A–D clearly demonstrate that the H-Ras/PI3K/Akt pathway downregulates RhoB at the promoter as well as the protein levels. If downregulation of RhoB is a critical step for the H-Ras/PI3K/Akt pathway to mediate malignant transformation, then ectopic expression of RhoB should antagonize this transformation. To evaluate this possibility, NIH3T3 cells were transfected with DNA constructs containing RhoA, RhoB, H-Ras61L, CAPI3K, and CA-Akt, either alone or in combination, the ability of these cells to form foci was followed as described in the Materials and Methods section. FIG. 8A shows that parental NIH3T3 cells, as expected, grew no colonies, but those transfected with either H-Ras61L, CA-PI3K or CAAkt grew numerous colonies. Co-transfection with RhoB but not RhoA along with the above genes resulted in significant inhibition of colony formation (see actual colony numbers in FIG. 8A).

EXAMPLE 15

The ability of oncogenic H-Ras, CA-PI3K and CA-Akt to induced migration is inhibited by RhoB not RhoA.

Figure 8B:
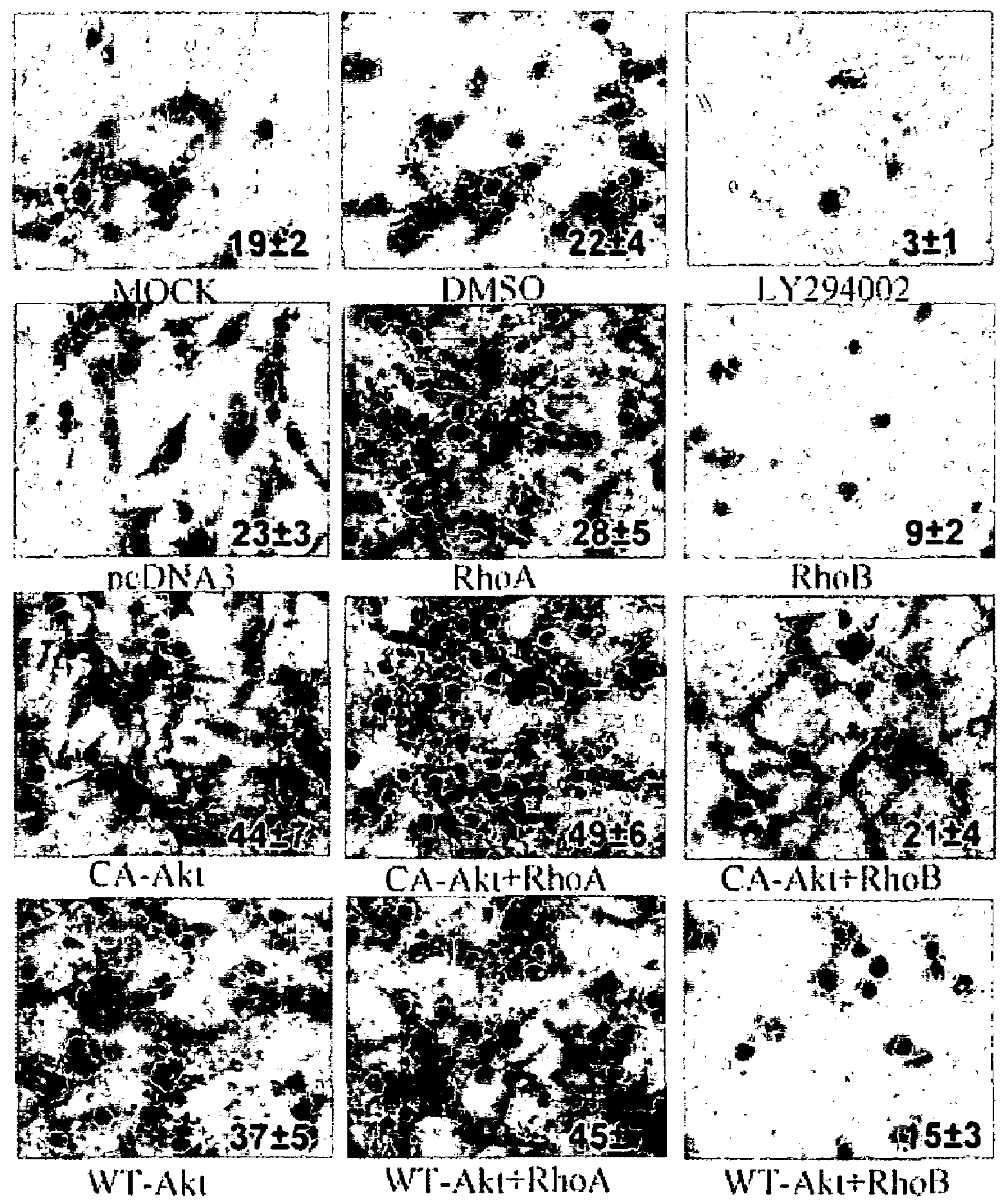
Figure 8C:
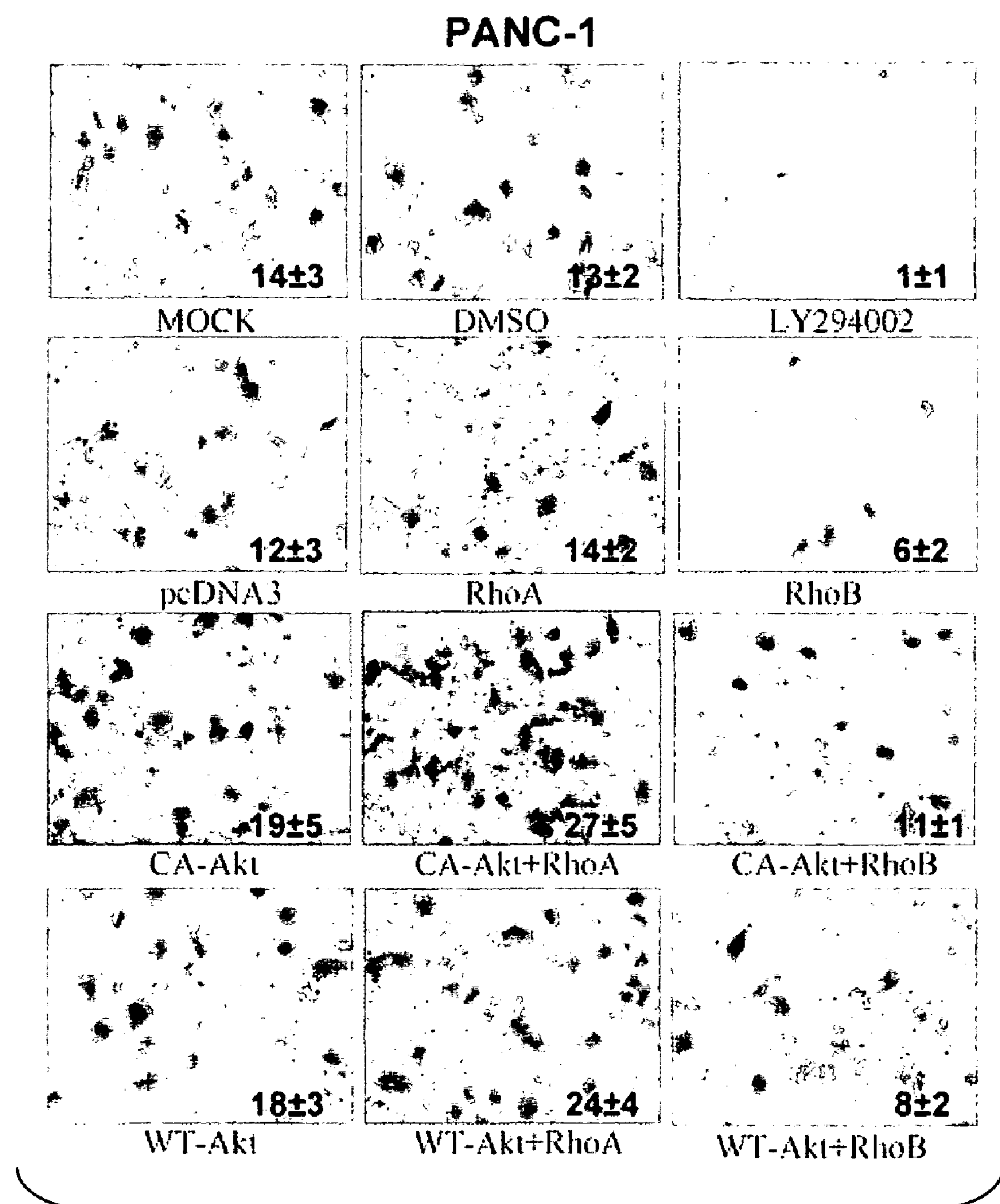

Among the hallmarks of malignant transformation is the ability of cancer cells to migrate, invade and metastasize, and the Ras/PI3K/Akt pathway is well known to be intimately involved in these processes (Arboleda, M. J. et al., *Cancer Res,* 2003, 63:196–206; Stewart, A. L. et al., *Mol Med,* 2002, 8:451–61; Davies, M. A. et al., *Clin Cancer Res,* 2002, 8:1904–14; Park, B. K. et al, *Cancer Res,* 2001, 61:7647–53; Kubiatowski, T. et al., *J Neurosurg,* 2001, 95:480–8; Kim, D. et al., *Faseb J,* 2001, 15:1953–62). Based on the results shown in FIGS. 5A–5D, 6A–6D, and 7A–7F, it was reasoned that Ras/PI3K/Akt may have to suppress RhoB to induce migration and invasion and therefore, ectopic RhoB expression may block the ability of this pathway to induce migration and invasion. To further explore this possibility, whether RhoB inhibits Ras/PI3K/Akt-induced cellular migration was examined. To this end, oncogenic H-Ras transformed NIH3T3 cells and PANC-1 cells were analyzed for their capabilities to migrate through collagen type I in the presence or absence of ectopically expressed RhoA or RhoB as described in the Materials and Methods section. FIGS. 8B and 8C show that mock pcDNA3 and RhoA-transfected, as well as DMSO-treated cells, migrated (through collagen type I) to the lower side of the transfilter. In contrast, the ability of LY294002-treated H-Ras/3T3 and PANC-1 cells, as well as cells transfected with RhoB, was dramatically hindered (FIGS. 8B and 8C). Furthermore, CA-Akt or WT-Akt alone or with RhoA enhanced the ability to migrate, while RhoB inhibited the ability of CA-Akt and WT-Akt to enhance cell migration (FIGS. 8B and 8C).

Figure 8D:
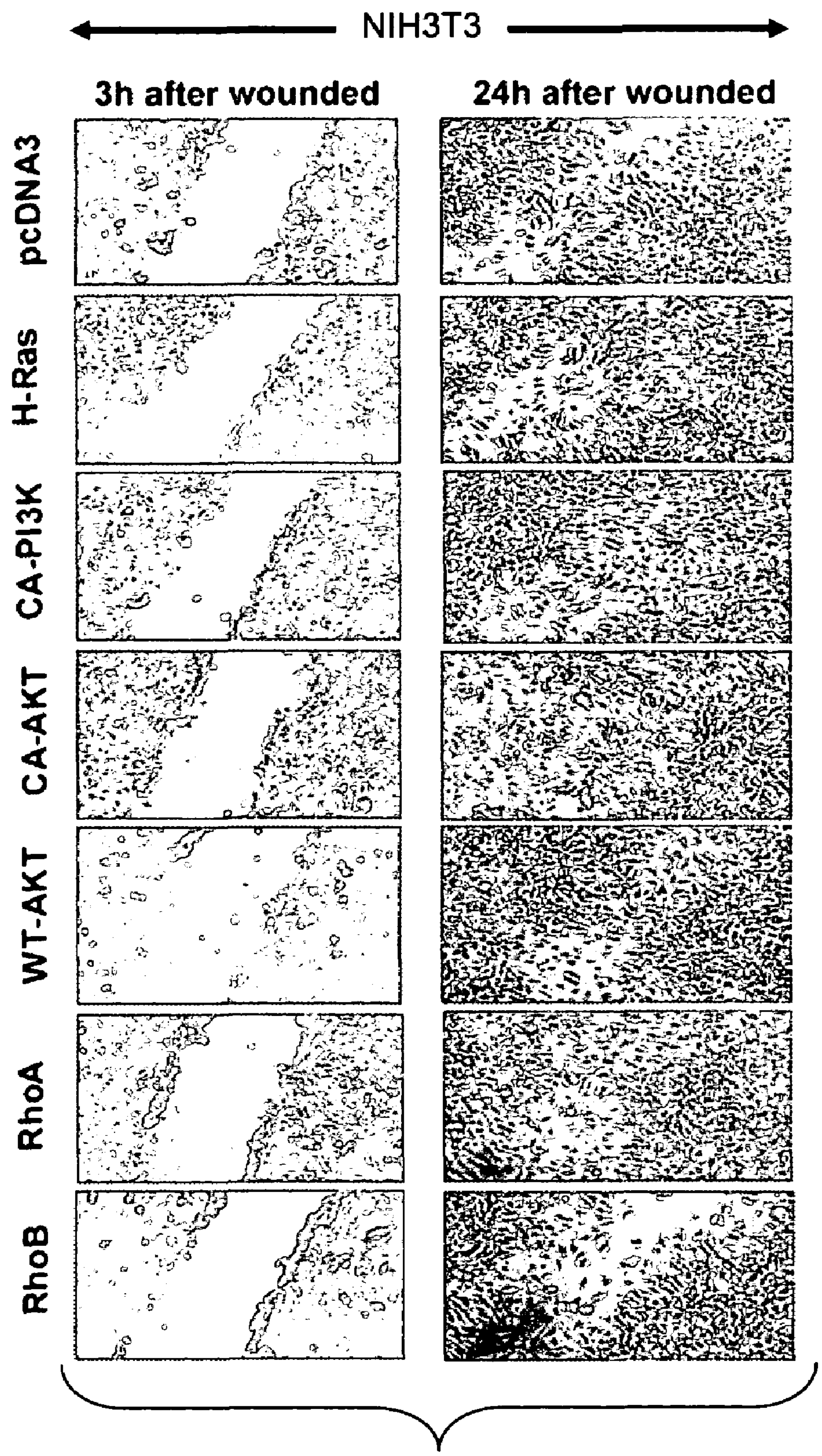
Figure 8E:
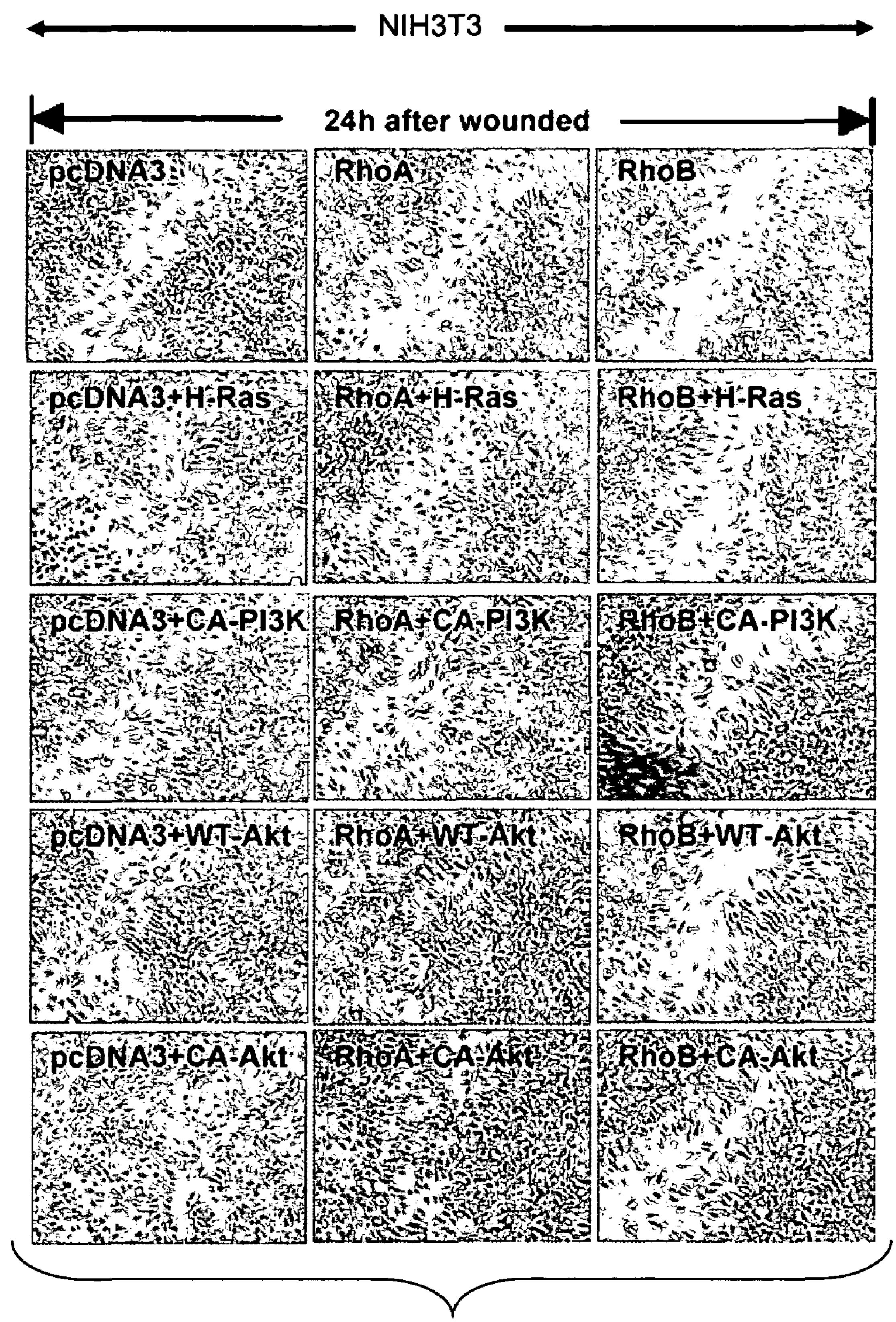

The ability of RhoB to inhibit cancer cell migration was further confirmed in a different assay where cells are induced to migrate by physical wounding of cells plated on fibronectin pre-coated plates. FIG. 8D shows that 24 hours after wounding, NIH3T3 cells transfected with pcDNA3 were able to grow and fill the wounded area. FIG. 8D also shows that oncogenic H-Ras, CA-PI3K, CA-Akt, WT-Akt, and RhoA transfection accelerated, whereas RhoB inhibited, the wound healing. Furthermore, RhoB also inhibited the ability of oncogenic H-Ras, CA-PI3K, CA-Akt, and WT-Akt to enhance wound healing (FIG. 8E).

EXAMPLE 16

RhoB, not RhoA, inhibited H-Ras/PI3K/Akt mediated cell invasion

Figure 9A:
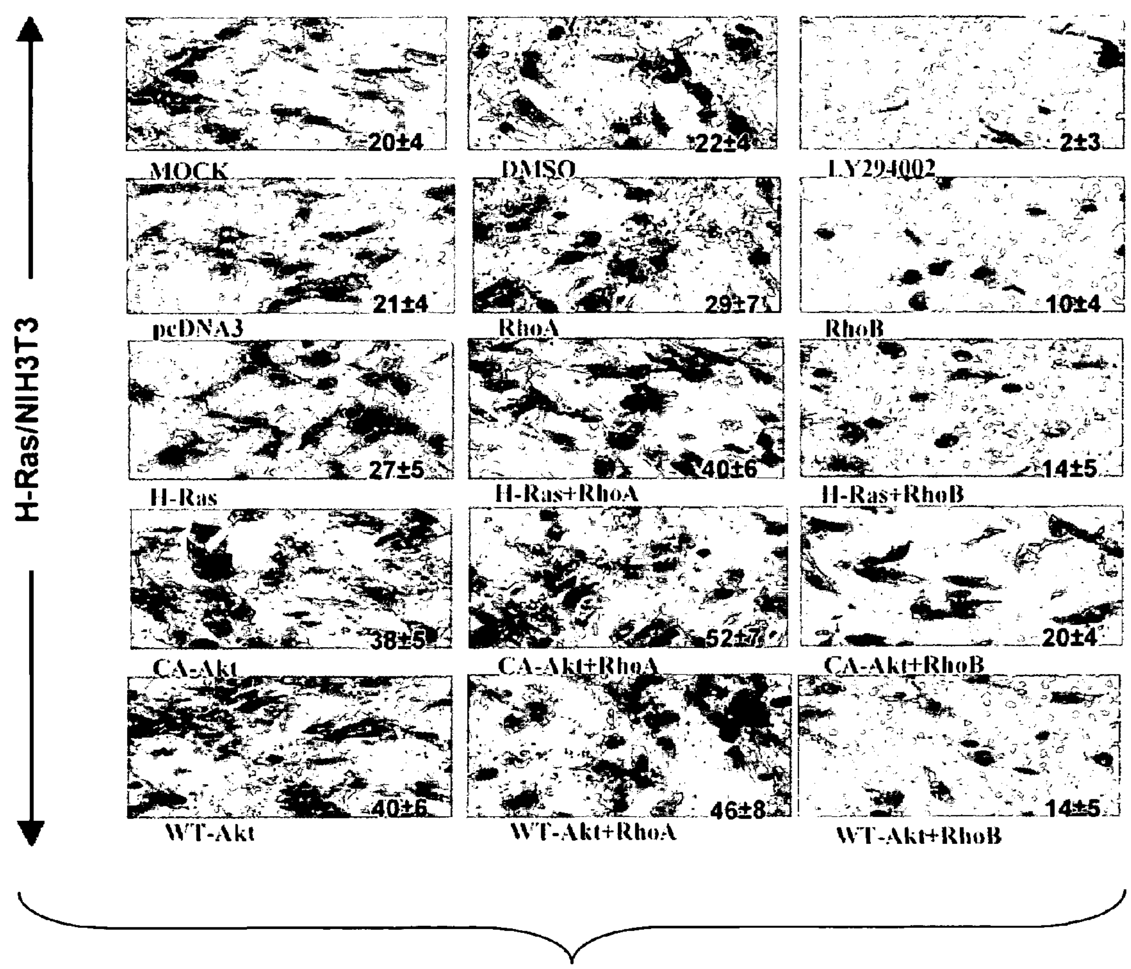
FIGS. 9A–9C show that RhoB, but not RhoA, inhibits H-Ras/PI3K/Akt-mediated cell invasion. HRas/3T3 cells (FIG. 9A) and PANC-1 cells (FIG. 9B) were transiently transfected with pcDNA3 vector control, H-Ras61L, CA-Akt, or WT-Akt in the presence or absence of RhoA, RhoB, or pcDNA3 for 36 hours. The cells were then split and analyzed for their invading capabilities through MATRIGEL-coated transfilters as described in the Materials and Methods section. PANC-1 and PC3 cells (FIG. 9C) were transiently transfected with pcDNA3, with H-Ras61L in the presence or absence of RhoA, or RhoB for 36 hours. The cells were then serum-starved for another 36 hours; the conditioned medium was collected and 20 μg protein were analyzed for MMP-2 expression by Western Blotting.
Figure 9B:
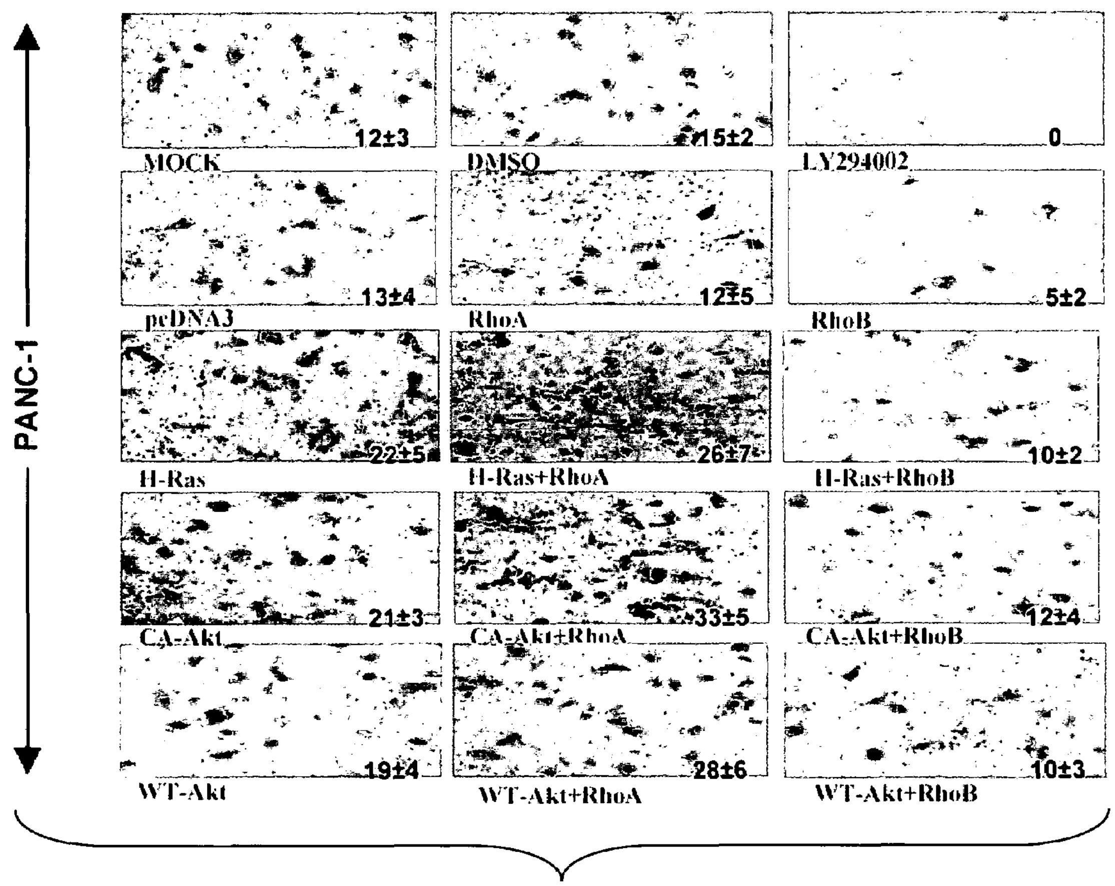

The results shown in FIGS. 8A–8E demonstrate that ectopic expression of RhoB antagonizes cell migration. Whether RhoB can also antagonize cell invasion was evaluated. To this end, H-Ras/3T3 and PANC-1 cells were similarly transfected as above with various oncogenes along with RhoA or RhoB, then seeded onto MATRIGEL-coated polyhydrocarbonate filters mounted in the middle of a Boyden transwell apparatus as described under Methods. FIGS. 9A and 9B show that mock-transfected or DMSO-treated cells efficiently invaded through MATRIGEL/collagen. In contrast, LY294002-treated H-Ras/3T3 and PANC-1 cells did not invade. In addition, cells transfected with pcDNA3, pcDNA3-RhoA, but not pcDNA3-RhoB, invaded. Furthermore, transfection with CA-Akt or WT-Akt enhanced invasion; and RhoB, not RhoA, inhibited this enhancement of invasion (FIGS. 9A and 9B).

EXAMPLE 17

RhoB, not RhoA, inhibits the expression of MMP-2 in human cancer cell lines

Figure 9C:
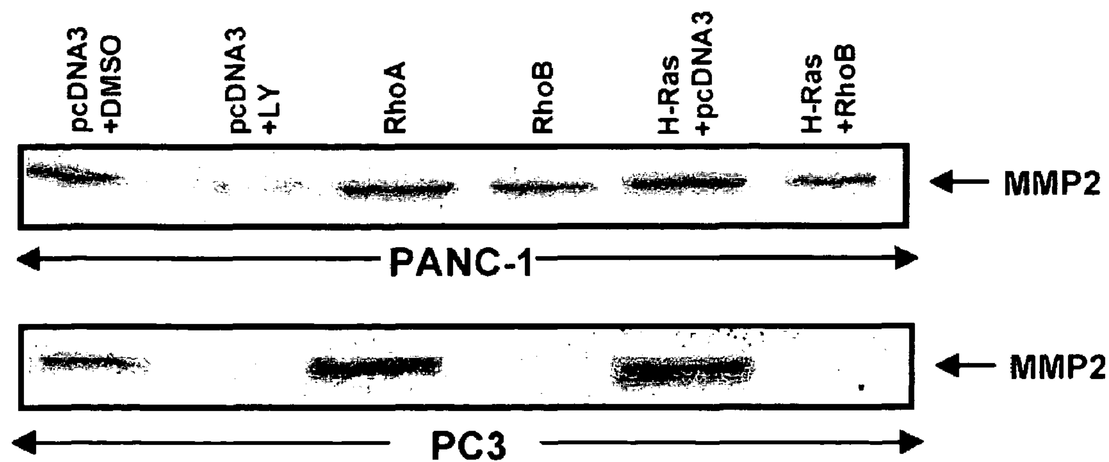

FIGS. 8A–8E and 9A–9C demonstrate that RhoB inhibits H-Ras/PI3K/Akt mediated cell migration and invasion, respectively. One pivotal step in these processes is the ability of cancer cells to cut through the extracellular matrix. This is accomplished by a cascade of proteinases, among which matrix metalloproteinases (MMPs) play a pivotal role (Yoon, S. O. et al., *J Biochem Mol Biol,* 2003, 36:128–37; Stamenkovic, I. *Semin Cancer Biol,* 2000, 10:415–33). Therefore, it was reasoned that since RhoB does block cell migration and invasion, it may do so at least in part by inhibiting MMP(s) expression. To this end, PANC-1 and PC3 cells were treated with LY294002, or transfected with pcDNA3-RhoA or RhoB, and the conditioned culture medium was collected and analyzed for MMP-2 expression by anti-MMP-2 Western blotting as described in the Materials and Methods section. FIG. 9C shows that pcDNA3-transfected and DMSO-treated PANC-1 and PC3 cells secrete basal level of MMP-2, which was decreased by LY294002, implicating the critical roles played by PI3K signaling in MMP-2 expression. Furthermore, H-Ras transfection significantly increased MMP-2 production and RhoA transfection also increased MMP-2 levels, but to a lesser extent. In contrast, RhoB transfection remarkably reduced not only the basal, but also the induced levels of MMP-2 protein secreted by these cancer cells especially in PC3 cells (FIG. 9C).

EXAMPLE 18

Figure 10A:
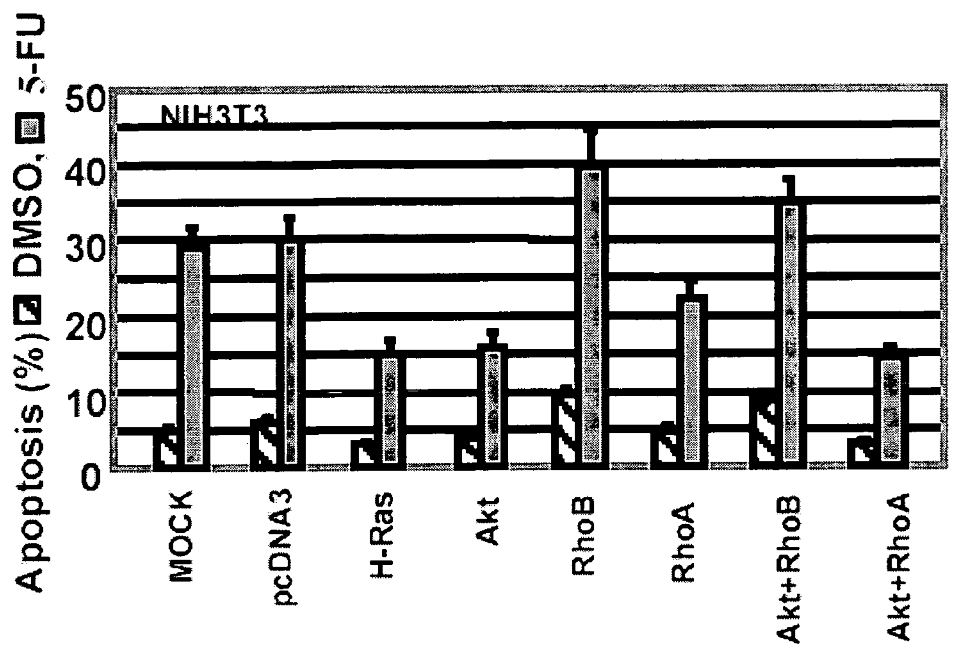
FIGS. 10A–10E show that RhoB, but not RhoA, inhibits H-Ras/PI3K/Akt-mediated cell survival and metastasis. Parental NIH3T3 cells (FIG. 10A) were transiently transfected with pcDNA3 vector, HRas61L, or Akt in the presence or absence of RhoA, RhoB, or pcDNA3 for 36 hours. The cells were then split and cultured in DMEM medium containing 2 μM 5-FU for another 48 hours. The cells were then examined for their susceptibility to 5-FU-induced apoptosis by Annexin V labeling and flow cytometry apoptosis assays as described in the Materials and Methods section. 36 hours after the transfection, a fraction of the cells from FIG. 10A were washed and re-suspended in serum-free medium and seeded into the pre-coated plates and examined for viability at different time points by Annex V and 7-AAD labeling, as shown in FIG. 10B.

RhoB, not RhoA, reverses Ras/PI3K/Akt-mediated resistance to 5-FUinduced apoptosis and protects against anoikis Another hallmark of cancer cells is to resist apoptosis and promote tumor survival. The ability of 5-FU to induce RhoB is antagonized by the Ras/PI3K/Akt pathway (FIGS. 6A–6D and 7A–7F), coupled with the previously reported role of RhoB in apoptosis (Chen, Z. et al., *J Biol Chem,* 2000, 275:17974–8; Liu, A. et al., *Proc Natl Acad Sci USA,* 2001, 98:6192–7), prompted the present inventor to determine the role of RhoB and the Ras/PI3/Akt pathway in 5-FU-induced apoptosis. To this end, NIH3T3 cells were transiently transfected with pcDNA3, H-Ras, Akt, RhoA, or RhoB for 24 hours and treated with DMSO vehicle or 5-FU for an additional 48 hours and apoptosis analyzed by Annexin V labeling and flow cytometry as described under Methods. FIG. 10A shows that 5-FU treatment induced 28–30% apoptosis in NIH3T3 cells. Transfection with H-Ras or Akt decreased the 5-FU apoptotic rate to 15% or 17%, respectively. Furthermore, while RhoA slightly protected, RhoB enhanced, the ability of 5-FU to induce apoptosis (FIG. 10A). Importantly, RhoB, but not RhoA, reversed Akt-mediated resistance to 5-FU-induced apoptosis.

Figure 10B:
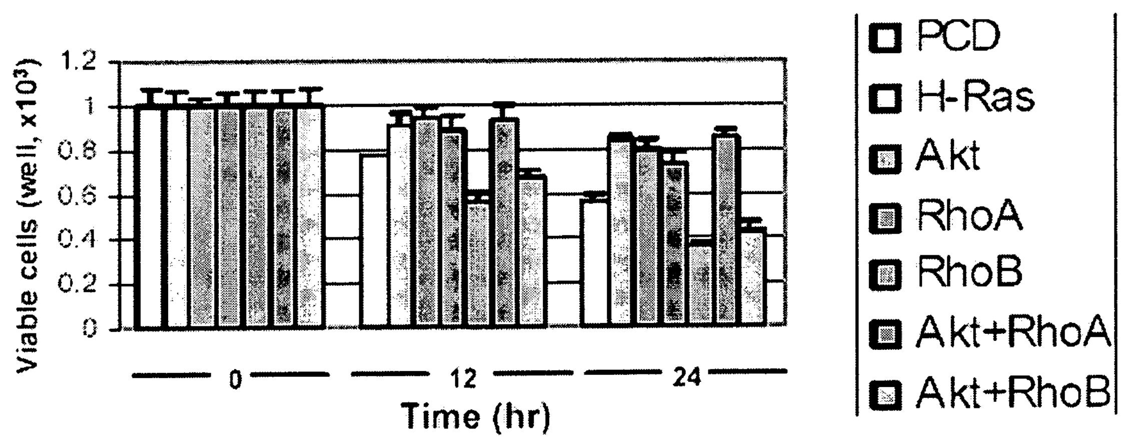

In addition to 5-FU-induced apoptosis, the effects of RhoB on apoptosis induced by depriving cells from substratum attachment (anoikis) was also examined. FIG. 10B shows that 12 hours or 24 hours after seeding into poly-HEMA-coated culture plates, RhoB-transfected cells displayed significantly higher cell death induced by lack of attachment than pcDNA3-transfected cells. However, H-Ras, Akt-, and RhoA-transfected cells showed a much lower rate of anoikis. Notably, RhoB reversed Akt-mediated resistance to this type of apoptosis (FIG. 10B).

EXAMPLE 19

RhoB, not RhoA, inhibits melanoma metastasis to the lung in a mouse model

Figure 10C:
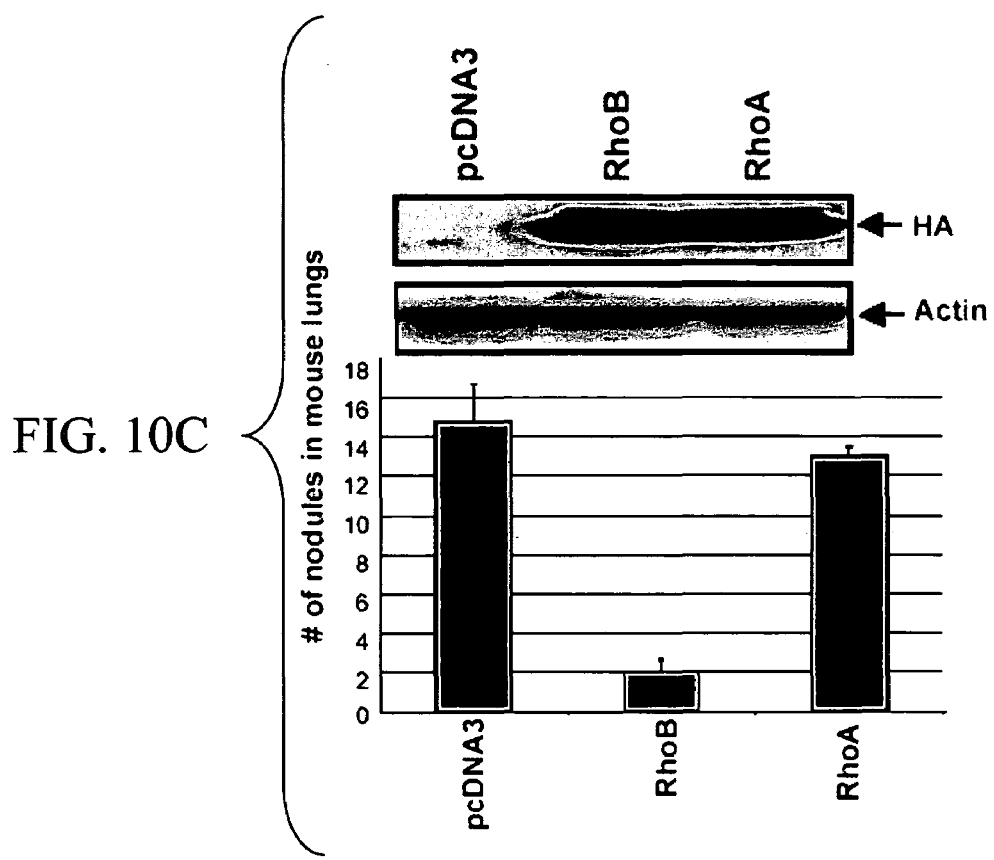
Figure 10D:
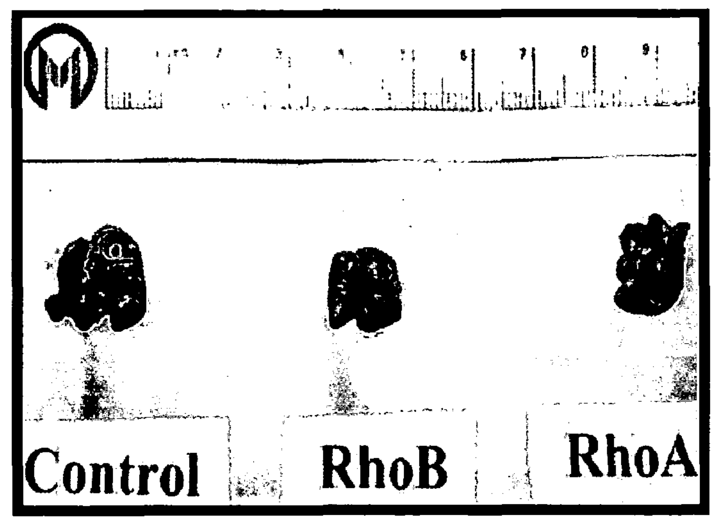
Figure 10E:
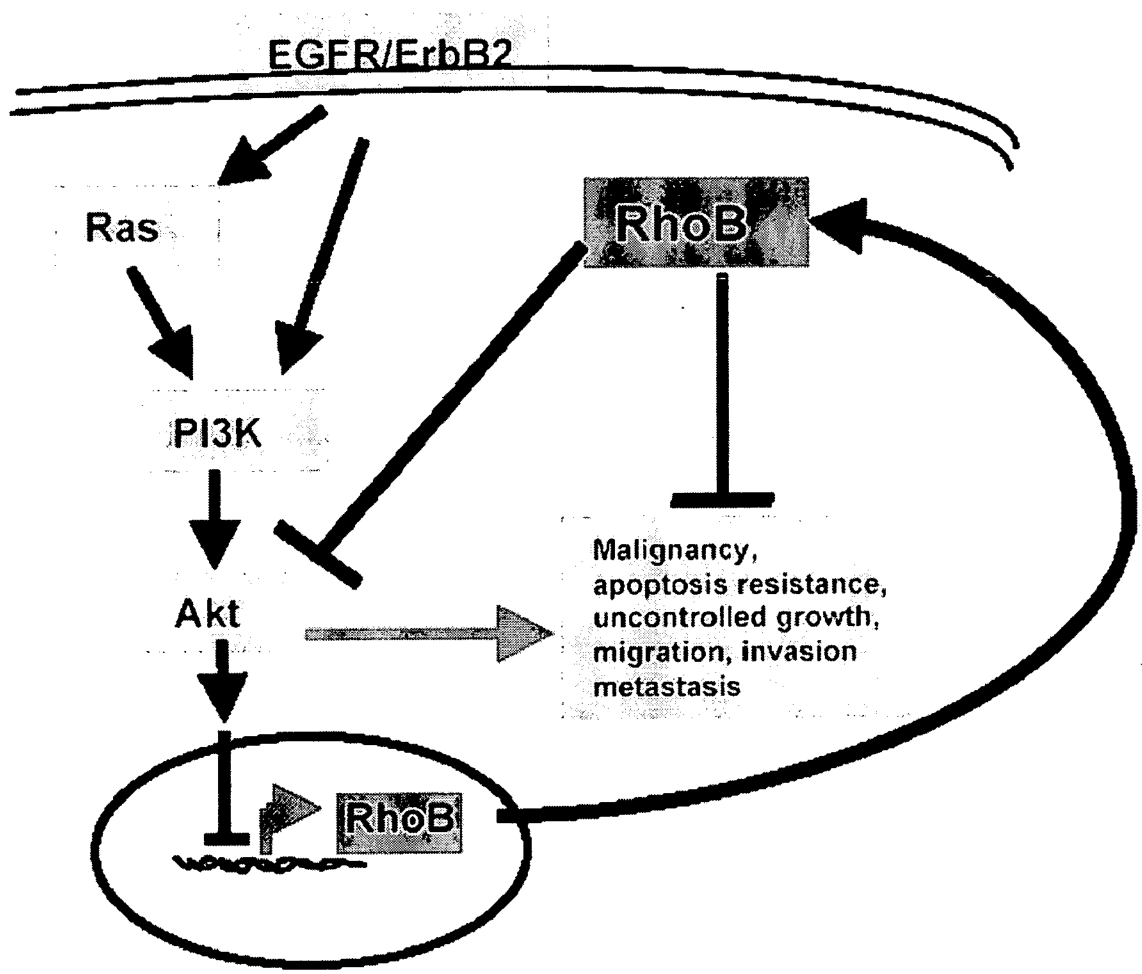

The work described above clearly shows that in cultured cells RhoB is a potent suppressor of transformation, migration, and invasion of cancer cells. To give further support to this in vivo, the highly metastatic melanoma cells B16-F10 were transfected with either pcDNA3, pcDNA3-RhoA, or pcDNA3-RhoB, and injected into the tail vein of C57 black mice. Lung metastasis was then determined after 3 weeks as described in the Materials and Methods section. FIG. 10C shows that transfected RhoA and RhoB were readily expressed in B16-F10 cells as determined by Western Blotting. FIG. 10D shows that pcDNA3-transfected cells were highly metastatic and grew 14.8±1.9 metastatic colonies per lung. Similarly, pcDNA3-RhoA-transfected B16 cells grew 13±4.5 colonies per lung. In contrast, pcDNA3-RhoB-transfected B16 cells grew only 2±0.7 colonies.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method for inhibiting the growth of a tumor cells in a mammal wherein the tumor cells are transformed by at least one oncogene selected from the group consisting of H-Ras, N-Ras, K-Ras, EGFR, and ErbB2, comprising directly administering an effective amount of a nucleic acid sequence encoding a wild-type RhoB protein to the tumor cells, wherein the nucleic acid sequence is expressed in the tumor cells.

2. The method of claim 1, wherein said method further comprises administering an additional anti-cancer agent to the tumor cells.

3. The method of claim 2, wherein the additional anti-cancer agent comprises a cytotoxic agent or an anti-signaling agent.

4. The method of claim 2, wherein the RhoB protein sensitizes the tumor cells to the anti-cancer agent.

5. The method of claim 1, wherein the nucleic acid sequence is associated with a pharmaceutically acceptable carner.

6. The method of claim 1, wherein the tumor cells are cells of a solid tumor mass.

7. The method of claim 1, wherein the tumor cells are not v-src trnsformed cells.

8. The method of claim 1, wherein the tumor cells are cells of a type selected from the group consisting of pancreatic cancer, prostate cancer, breast cancer, colon cancer, rectal cancer, lung cancer, head and neck cancer, and melanoma cancer.

9. The method of claim 1, wherein the tumor cells are lung cancer cells.

10. The method of claim 1, wherein the mammal is human.

11. The method of claim 1, wherein said administering comprises administering a viral vector containing the nucleic acid sequence to the tumor cells.

12. The method of claim 11, wherein the viral vector is adenovirus.

13. The method of claim 11, wherein the viral vector is adenovirus and the tumor cells are lung cancer cells.

14. The method of claim 1, wherein the tumor cells are liver cancer cells.

15. The method of claim 1, wherein the tumor cells are head and neck cancer cells.

16. The method of claim 1, wherein the tumor cells are melanoma cells.

* * * * *

UNITED STATES PATENT AND TRADEMARK OFFICE

CERTIFICATE OF CORRECTION

PATENT NO. : 7,135,463 B2
APPLICATION NO. : 10/759328
DATED : November 14, 2006
INVENTOR(S) : Said M. Sebti It is certified that error appears in the above-identified patent and that said Letters Patent is hereby corrected as shown below:

Column 4,
Line 49, "and 13-actin" should read --and β-actin--.

Column 25
Line 25, "carner" should read --carrier--.

Signed and Sealed this

Tenth Day of April, 2007

JON W. DUDAS
*Director of the United States Patent and Trademark Office*

UNITED STATES PATENT AND TRADEMARK OFFICE

CERTIFICATE OF CORRECTION

PATENT NO. : 7,135,463 B2
APPLICATION NO. : 10/759328
DATED : November 14, 2006
INVENTOR(S) : Said M. Sebti It is certified that error appears in the above-identified patent and that said Letters Patent is hereby corrected as shown below:

Column 26
Lines 6-7, "melanoma cancer." should read --melanoma.--.

Signed and Sealed this

Twenty-sixth Day of June, 2007

JON W. DUDAS
*Director of the United States Patent and Trademark Office*